United States Patent
Lu

(10) Patent No.: US 10,537,521 B2
(45) Date of Patent: Jan. 21, 2020

(54) INTRAVENOUS ADMINISTRATION OF TRAMADOL

(71) Applicant: Revogenex Ireland Ltd, Dublin (IE)

(72) Inventor: Lucy Lu, New York, NY (US)

(73) Assignee: Revogenex Ireland Ltd., Dublin (IE)

( * ) Notice: Subject to any disclaimer, the term of this patent is extended or adjusted under 35 U.S.C. 154(b) by 0 days.

(21) Appl. No.: 16/007,464

(22) Filed: Jun. 13, 2018

(65) Prior Publication Data

US 2018/0360741 A1    Dec. 20, 2018

Related U.S. Application Data

(63) Continuation of application No. 15/486,903, filed on Apr. 13, 2017, now Pat. No. 10,022,321.

(60) Provisional application No. 62/356,655, filed on Jun. 30, 2016.

(51) Int. Cl.
     *A61K 9/00*      (2006.01)
     *A61K 31/135*      (2006.01)

(52) U.S. Cl.
     CPC .......... *A61K 9/0019* (2013.01); *A61K 31/135* (2013.01)

(58) Field of Classification Search
CPC .. A61K 31/137; A61K 31/485; A61K 9/0019; A61K 9/0053
See application file for complete search history.

(56) References Cited

U.S. PATENT DOCUMENTS

2013/0005821 A1*   1/2013   Kottayil ............... A61K 31/485
                                                     514/646

FOREIGN PATENT DOCUMENTS

WO    WO 2012142273    * 10/2012

* cited by examiner

*Primary Examiner* — Umamaheswari Ramachandran
(74) *Attorney, Agent, or Firm* — Davidson, Davidson & Kappel, LLC

(57) ABSTRACT

A method of treating pain, e.g., acute post-operative pain, by administering to a human patient(s) a therapeutically effective dose of tramadol intravenously in a dosing regimen which includes one or more loading doses administered at shortened intervals as compared to dosing at steady-state is disclosed. In certain embodiments, the dose of tramadol about 25 mg and the second (and optionally) third doses are intravenously administered at intervals of about 2 hours, and thereafter the tramadol is intravenously administered at a dosing interval of about 4 hours, until the patient no longer requires treatment with tramadol.

20 Claims, 4 Drawing Sheets

INTRAVENOUS ADMINISTRATION OF TRAMADOL

This application is a continuation of U.S. application Ser. No. 15/486,903 filed Apr. 13, 2017.

BACKGROUND OF THE INVENTION

Tramadol is a centrally acting synthetic analgesic with a dual mechanism of action attributed to the racemic form of the drug, comprised of μ-opioid activity (binding to μ-opioid receptors and monoamine (serotonin and noradrenalin) reuptake inhibition. Tramadol is an analog of the phenanthrene group of opium alkaloids, which includes morphine and codeine, and is structurally related to these opioids (Grond S and Slabotzi A. Clinical pharmacology of tramadol. Clin Pharmacokinet. 2004; 43:879-923). Like codeine, there is a substitution of the methyl group on the phenol ring that imparts a relatively weak affinity for opioid receptors. (+)-Tramadol is a more potent inhibitor of serotonin uptake, while (−)-tramadol is a more potent inhibitor of norepinephrine uptake. The opioid-like activity of tramadol derives from low affinity binding of the parent compound to μ-opioid receptors and higher affinity binding of its main metabolite. Tramadol affinity to μ opioid receptors is about 10 times weaker than codeine 60 times weaker than dextropropoxyphene and 6,000 times weaker than morphine. The active metabolite O-desmethyltramadol (M1) possesses a higher affinity to the μ opioid receptor than tramadol and displays analgesic activity (Leppert W, 2009).

Tramadol was originally developed by the German pharmaceutical company Grünenthal GmbH in the late 1970s and is marketed globally under the trade names TRAMAL® and others outside of the United States. The approved doses of tramadol are 50 mg or 100 mg administered as a slow injection every 4-6 hours (Tramadol Core Product Label, 2008). In the U.S., tramadol is approved by the Food and Drug Administration (FDA) and marketed as an oral capsule/tablet for moderate to moderately severe pain in adults. Tramadol was first approved in the US in April 1995 under the trade name, ULTRAM® (Ortho-McNeil-Janssen Pharmaceuticals, Inc). Tramadol is also an active agent in an extended release product, Ultram® ER, and a combination product with acetaminophen, ULTRACET®. In the US, tramadol is only available as immediate release tablets or extended release tablets. Other tramadol formulations approved in several countries include tablets, capsules, effervescent powders, and suppositories (Grond and Sablotzki, 2004; Rosenberg, 2009). The approved intravenous regimen in India is an initial injection of 50 mg infusion over 2-3 min, followed by 50 mg every 10-20 minutes if necessary up to 250 mg for the first hour. Maintenance doses are 50-100 mg every 4-6 hours with a maximum dose of 600 mg daily (Tramadol, CIMS Data_India).

Postoperative pain management with tramadol has effectively utilized a variety of delivery methods, including bolus injection (IV or IM), continuous infusions and patient controlled analgesia (PCA) pumps, and various combinations of these methods (Scott and Perry, 2000; Grond and Sablotzki, 2004). The potency ratio of IV tramadol to IV morphine is approximately 1:10, while the ratio for IV fentanyl is 1:979 (Grond and Sablotzki, 2004).

The "on-demand" analgesic efficacy of tramadol was compared to morphine in the 24-hour post-operative period for 523 patients undergoing abdominal surgery (Vickers M D, Paravicini D. Comparison of tramadol with morphine for post-operative pain following abdominal surgery. Eur J Anesthesiol. 1995; 12: 265-71). Patients who reported postoperative pain received an initial dose (either tramadol 100 mg or morphine 5 mg i.v.) and, if necessary, repeat i.v. or i.m. doses of tramadol 50 mg or morphine 5 mg on demand over the first 90 minutes. Further doses up to a total of 400 mg tramadol or 40 mg morphine could then be given after 90 minutes up to 24 hours after the first dose of study medication. The primary efficacy parameter was the responder rate (no or slight pain) within the first 90 minutes of treatment. Responder rates were 72.6% for tramadol and 81.2% for morphine, which were statistically equivalent and within the predefined range of ±10%. Mean cumulative doses were 188.2 mg for the first 90 minutes and 157.1 mg for the subsequent 22.5 hours in the tramadol group and 13.9 mg and 18.4 mg, respectively in the morphine group. The main adverse events were gastrointestinal in both groups, with mild nausea, dry mouth, vomiting, dyspepsia and hiccups reported most frequently.

The analgesic effect of continuous infusion of tramadol was compared to repeated bolus administration in 135 patients undergoing abdominal surgery (Rud U, Fischer M V, Mewes R, Paravcini D., "Postoperative Analgesie mit Tramadol Kontinuierliche Infusion versus repetitive" (Post-operative analgesia with tramadol. Continuous infusion versus repetitive bolus administration), Bolusgabe Anaesthesist. 1994; 43:316-321. (German)). Patients were randomized at the time of the first request for pain treatment. All patients received a loading dose of tramadol 100 mg i.v. Subsequent treatment was administered in a double-blind manner; patients in the infusion group were given a continuous infusion of tramadol 12 mg/h for 24 hours, whereas patients in the bolus group received placebo infusion. In both groups, additional bolus doses of tramadol 50 mg i.v. were given as required. Pain relief was monitored by means of a visual analog scale (VAS) up to 6 hours after surgery. The number of additional boluses and the amount of tramadol administered at 6 hours and 24 hours was also used to assess analgesic efficacy. More patients in the infusion group assessed their pain relief as excellent or good compared to the bolus group (76.5% vs 65.6%). Only a few patients complained of insufficient analgesia, with more patients in the bolus group reporting inadequate pain relief than in the infusion group (7.5% vs 4.4%). A higher percentage of patients in the bolus group required two or more boluses compared to the infusion group (59.7% vs 30.8%). After 6 hours, the average tramadol consumption was 223.5±53.7 mg in the infusion group and 176.6±63.1 mg in the bolus group (p<0.05). After 24 hours, tramadol consumption was 449.5±66.0 mg and 201.6±83.9 mg (p<0.001), respectively. Adverse events were reported by 25% of patients in both groups, with no significant differences and no patient terminated the trial for an adverse event. There were no significant effects on blood pressure or heart rate. The authors concluded that continuous infusion was more effective in the first 6 hours after surgery. However, excess consumption by the infusion group was statistically greater than the bolus group at both 6 hours and 24 hours postsurgery.

Intermittent bolus and continuous infusion of tramadol were evaluated in a postoperative study of 35 patients undergoing major abdominal gynecologic surgery (Chrubasik J, Buzina M, Schulte-Monting J, Atanassoff P, Alon E. Intravenous tramadol for post-operative pain-comparison of intermittent dose regimens with and without maintenance infusion. Eur J Anaesthesiol. 1992; 9:23-28). The study was randomized and double-blind and used tramadol infusion 15 mg/h or saline. Additional boluses of tramadol 100 mg were given as requested. The patients in the infusion group required 60% less tramadol on demand (p<0.01) and had better pain relief (p<0.05), as assessed by VAS, than the group that received the saline infusion. Total tramadol consumption, however, was about 30% higher in the infusion group (p<0.05) and was associated with and increased incidence of minor adverse events. Tramadol was ineffective as pain relief within 2 hours of the beginning of treatment in 6% of the infusion group and 20% of the bolus group. Thus, continuous infusion was preferred to "on-demand" bolus treatment.

A meta-analysis of nine randomized, controlled trials indicated that tramadol was as effective as other opioids, including morphine, for control of postoperative pain (Scott and Perry, 2000). Pain in these patients was described as moderate to severe, with initial postoperative pain reported as >60 on a 100-point visual analog scale or as moderate or severe on a 4- or 5-point verbal response scale. The first dose of analgesia was administered when patients reported moderate to severe pain in the postoperative setting. Studies that did not adequately record baseline pain severity or response to analgesia, were not randomized or controlled or contained less than 45 patients were excluded from the meta-analysis. Tramadol, administered in a dose titrated to pain response and via either IV (intravenous) or IM (intramuscular) intermittent injection, reduced pain intensity by 46.8% to 57.6% after 4 to 6 hours compared to 69.8% for morphine and 25.6% to 51.3% for pentazocine. Efficacy of tramadol was maintained for the duration of the studies, which were <72 hours, and was comparable to morphine or alfentanil. However, the onset of action of tramadol was slower than morphine, as assessed by measurements approximately 3 hours after the first dose. There were no significant differences in the percentage of patients treated with tramadol or morphine and who also required rescue medication. The patient global response and physician global response were similar for tramadol and for other opioids.

Tramadol injection (IV/IM/SC) is approved and used for the management of moderate to severe acute postoperative pain in several regions, including Europe, India and Australia/New Zealand (however, this dosage form is not available in the USA). Tramadol ampoules or vials for IV, IM and SC administration are preservative-free solutions for injection by the various spinal routes (epidural, intrathecal, caudal, etc.) are available forms in these regions. Tramadol formulations approved in several countries include, tablets, capsules, effervescent powders, and suppositories (Grond and Sablotzki, 2004; Rosenberg, 2009).

There is extensive data demonstrating that tramadol use is not associated with the classical opioid side effects seen with more potent opioids. There are numerous reports of the safety and efficacy of tramadol (Lee et al., 1993; Scott and Perry, 2000; Grond and Sablotzki, 2004). The most common adverse events of tramadol administration are nausea, dizziness, headache, somnolence, sweating, fatigue, constipation, dry mouth and vomiting. However, tramadol use, particularly with high doses, has been associated with seizures, and the risk of seizures is increased in the presence of drugs that reduce seizure threshold, head trauma or prior history of seizures.

Patients undergoing surgery, for example, total knee arthroplasty (TKA) and total hip arthroplasty (THA), typically demonstrate a need for short-term analgesia, which is critical for earlier mobilization and rehabilitation. In this setting, assuring adequate pain relief without providing extensive medical oversight required for some methods of treatment (such as neuraxial anesthesia) and prevention of effects such as opiate-induced respiratory depression and dependency would be highly beneficial (Sinatra et al., 2002).

The goal of post-surgical pain management is twofold: i) to provide a quick onset of analgesic or pain relief and ii) to reduce or modulate the quality and intensity of pain that a patient experiences in the post-surgical period. While current treatments for management of post-surgical acute pain are useful, there is a need for improved methods for treating post-surgical acute pain.

OBJECTS AND SUMMARY OF THE INVENTION

It is an object of the present invention to provide a method of treating pain in human patients.

It is a further object of the present invention to provide a method of treating pain in human patients who are unable to take oral medications, such as in a post-operative condition.

It is a further object of the present invention to provide a method of treating pain in human patients that takes advantage of the faster onset of intravenous administration of tramadol while providing additional benefits not available via current methodologies of tramadol intravenous administration.

It is another object of the present invention to provide a method of providing a safe and effective alternative injectable analgesic for use in the acute postoperative setting.

It is another object of the present invention to provide a method for treating pain in, e.g., the acute postoperative setting which is or may be opioid-sparing.

It is another object of the present invention to provide a method for treating pain with intravenous tramadol in human patients in a manner that may or does reduce side-effects (such as, e.g., nausea, vomiting or seizure).

It is a further object of the present invention to provide a method of treating pain with a drug and dosing regimen that provides a positive benefit-risk profile, and which addresses an unmet medical need for the management of acute postoperative pain.

It is an object of the present invention to provide an intravenous dosing regimen for tramadol using a lower dose than that previously considered to be useful by those skilled in the art.

It is an object of the present invention to provide a dosing regimen for intravenous tramadol that provides treating physicians with a clear picture of what tramadol blood plasma levels they are obtaining in relation to oral tramadol (a drug that they are very familiar with).

In accordance with the above objects and others, the present invention is directed in part to a method of administering tramadol for treating pain via an intravenous dosing regimen comprising or consisting of intravenously administering a first dose of tramadol to a human patient in an amount of about 25 to less than 50 mg; intravenously administering a second dose of tramadol to the human patient in an amount from about 25 mg to about 50 mg at about 2 hours after the first dose; intravenously administering a third dose of tramadol to the human patient in an amount from about 25 mg to less than 50 mg at about 2 hours after the second dose; and thereafter intravenously administering from about 25 mg to less than 50 mg tramadol at dosage intervals of about 4 hours, until the patient no longer requires treatment with tramadol. In certain preferred embodiments, the intravenous dosing regimen provides a Cmax and AUC of tramadol which is similar to the Cmax and AUC of an oral dose of 50 mg tramadol HCl given every 6 hours at steady-state.

In certain preferred embodiments, the Cmax of the intravenous dose of 25 mg at 4 hours after administration of the first intravenous dose (i.e., after the third intravenous dose) is similar to the steady-state Cmax achieved with an oral tramadol dose of 50 mg administered every 6 hours (the Cmax of the oral tramadol dosing regimen not occurring until about 44 hours after the first dose). In certain preferred embodiments, the dose administered each time is about 25 mg. In certain preferred embodiments, the method comprises administering from about 175 mg to about 343 mg tramadol intravenously over an initial 24 hour period of treatment, and a daily dose from about 150 mg to about 294 mg daily thereafter.

The present invention is further directed in part to a method of administering tramadol for treating pain via an intravenous dosing regimen comprising or consisting of intravenously administering a first dose of tramadol to a human patient in an amount of about 25 mg; intravenously administering a second dose of tramadol to the human patient in an amount of about 25 mg at about 2 hours after the first dose; intravenously administering a third dose of tramadol to the human patient in an amount of about 25 mg at about 2 hours after the second dose; and thereafter intravenously administering about 25 mg tramadol at dosage intervals of about 4 hours, until the patient no longer requires treatment with tramadol. In certain preferred embodiments, the intravenous dosing regimen provides a Cmax and AUC of tramadol which is similar to the Cmax and AUC of an oral dose of 50 mg tramadol HCl given every 6 hours at steady-state. In certain preferred embodiments, the method comprises administering from about 200 mg tramadol intravenously over an initial 24 hour period of treatment, and a daily dose from about 175 mg daily thereafter.

The present invention is further directed in part to a method of administering tramadol for treating pain via an intravenous dosing regimen comprising or consisting of intravenously administering a first dose of tramadol to a human patient in an amount from about 25 mg to less than 50 mg; intravenously administering a second dose of tramadol to the human patient in an amount of about 50 mg or from about 25 mg to less than 50 mg at about 2 hours after the first dose; intravenously administering a third dose of tramadol to the human patient in an amount from about 25 mg to less than 50 mg (and in certain embodiments preferably about 25 mg) at about 2 hours after the second dose; and thereafter intravenously administering from about 25 mg to less than 50 mg tramadol (and in certain embodiments preferably about 25 mg) at dosage intervals of about 4 hours, until the patient no longer requires treatment with tramadol. In certain preferred embodiments, the intravenous dosing regimen provides a Cmax and AUC of tramadol which is similar to the Cmax and AUC of an oral dose of 50 mg tramadol HCl given every 6 hours at steady-state.

In other embodiments, the present invention is directed in part to a method of administering tramadol for treating pain via an intravenous dosing regimen comprising or consisting of intravenously administering a first dose of tramadol to a human patient in an amount of about 25 mg; intravenously administering a second dose of tramadol to the human patient in an amount from about 25 mg to about 50 mg or any tramadol dose in between those doses) at about 2 hours after the first dose; intravenously administering a third dose of tramadol to the human patient in an amount from about 25 mg to less than 50 mg (or any tramadol dose in between those doses) at about 2 hours after the second dose; and thereafter intravenously administering from about 25 mg to about 50 mg (or any tramadol dose in between those doses) tramadol at dosage intervals of about 4 hours, until the patient no longer requires treatment with tramadol. In certain preferred embodiments, the dose administered each time is about 25 mg. Preferably, the mean tramadol concentration for the intravenous dosing regimen provides similar steady-state peak and trough concentrations as compared to a dosing regimen of 50 mg tramadol HCl administered orally every 6 hours at steady-state. In certain preferred embodiments, the method comprises administering from about 175 mg to about 343 mg tramadol intravenously over an initial 24 hour period of treatment, and a daily dose from about 150 mg to about 294 mg daily thereafter.

In a preferred embodiment, the dosing regimen comprises or consists of 25 mg IV tramadol at hour 0, followed by 25 mg at hour 2, 25 mg at hour 4, and 25 mg every 4 hours thereafter (e.g., until the patient no longer requires treatment with intravenous tramadol, e.g. about 48 hours after the first dose (with the last intravenous dose being administered 44 hours after the first dose)).

The invention is further directed in part to a method of administering tramadol for treating pain in a human patient(s) via an intravenous dosing regimen, comprising intravenously administering a first dose of tramadol to a human patient(s) in an amount of about 25 mg; intravenously administering a second dose of tramadol to the human patient(s) in an amount of about 25 mg at about 2 hours after the first dose; intravenously administering a third dose of tramadol to the human patient(s) in an amount of about 25 mg at about 2 hours after the second dose; and thereafter intravenously administering additional doses of tramadol to the human patient(s) in an amount of about 25 mg tramadol at dosage intervals of about 4 hours, such that the mean Cmax concentration after administration of the third administered dose of tramadol is similar to the mean Cmax of the intravenous dosing regimen at steady-state and is similar to the Cmax at steady-state for a dosing regimen of 50 mg tramadol HCl administered orally every 6 hours, wherein the tramadol is tramadol base or a pharmaceutically acceptable salt of tramadol.

The invention is further directed in part to a method of administering tramadol for treating pain in a human patient(s) via an intravenous dosing regimen, comprising intravenously administering a first dose of tramadol to a human patient(s) in an amount of about 25 mg; intravenously administering a second dose of tramadol to the human patient(s) in an amount of about 25 mg at about 2 hours after the first dose; intravenously administering a third dose of tramadol to the human patient(s) in an amount of about 25 mg at about 2 hours after the second dose; and thereafter intravenously administering additional doses of tramadol to the human patient(s) in an amount of about 25 mg tramadol at dosage intervals of about 4 hours, such that the intravenous dosing regimen provides a Cmax of tramadol at steady-state from about 80% to about 125% of about 368 ng/mL (i.e., from about 294 ng/ml to about 460 ng/ml). Preferably, the Cmin of tramadol at steady-state via this intravenous dosing regimen is about 224±66 ng/ml, or from about 80% to about 125% of about 224 ng/ml (i.e., from about 179 to about 280 ng/ml).

The invention is further directed in part to a method of administering tramadol for treating pain in a human patient(s) via an intravenous dosing regimen, comprising intravenously administering a first dose of tramadol to a human patient(s) in an amount of about 25 mg; intravenously administering a second dose of tramadol to the human patient(s) in an amount of about 25 mg at about 2 hours after the first dose; intravenously administering a third dose of tramadol to the human patient(s) in an amount of about 25 mg at about 2 hours after the second dose; and thereafter intravenously administering additional doses of tramadol to the human patient(s) in an amount of about 25 mg tramadol at dosage intervals of about 4 hours, such that the peak/trough ratio of tramadol at about 44 hours after the first administered dose of tramadol is about 1.637±0.2655.

The invention is further directed in part to a method of administering tramadol for treating pain in a human patient(s) via an intravenous dosing regimen, comprising intravenously administering a first dose of tramadol to a human patient(s) in an amount of about 25 mg; intravenously administering a second dose of tramadol to the human patient(s) in an amount of about 25 mg at about 2 hours after the first dose; intravenously administering a third dose of tramadol to the human patient(s) in an amount of about 25 mg at about 2 hours after the second dose; and thereafter intravenously administering additional doses of tramadol to the human patient(s) in an amount of about 25 mg tramadol at dosage intervals of about 4 hours, such that the Cmax after the second dose is approximately 50% higher than Cmax after the first dose, and that the Cmax after the 3rd dose is approximately 50% higher than the Cmax after the second dose, and that the Cmax after further doses are comparable to Cmax after the 3rd dose. In certain preferred embodiments, the intravenous dosing regimen provides a Cmax and AUC of tramadol which is similar to the Cmax and AUC of an oral dose of 50 mg tramadol HCl given every 6 hours at steady-state.

In certain preferred embodiments, the intravenous dosing regimens of the invention provide a Cmax of tramadol at steady-state that is similar or substantially the same as the Cmax provided at steady-state by a 50 mg oral dose of tramadol HCl given every 6 hours.

In certain preferred embodiments, the intravenous dosing regimens of the invention provide a Cmax of tramadol at steady-state that is from about 80% to about 125% of the Cmax provided at steady-state by a 50 mg oral dose of tramadol HCl given every 6 hours.

In certain preferred embodiments, the intravenous dosing regimens of the present invention provide an AUC of tramadol at steady-state that is from about 80% to about 125% of the AUC provided at steady-state by a 50 mg oral dose of tramadol HCl given every 6 hours.

In certain preferred embodiments, the intravenous dosing regimens of the invention provide a Cmax of the M1 metabolite of tramadol at steady-state that is from about 20% to about 100% (in certain embodiments from about 60% to about 75%), or from about 80% to about 100% of the Cmax of the M1 metabolite of tramadol at steady-state when the tramadol is administered as oral 50 mg tramadol HCl every 6 hours.

In certain preferred embodiments, the intravenous dosing regimens of the invention provide an AUC of the M1 metabolite of tramadol at steady-state which is from about from about 20% to about 100% (in certain embodiments from about 60% to about 75%), or from about 80% to about 100% of the steady-state AUC of the M1 metabolite of tramadol when the tramadol is administered as oral 100 50 mg tramadol HCl every 6 hours.

In certain embodiments of the intravenous dosing regimens of the invention, the intravenous dosing regimen provides a Cmax of tramadol at steady-state from about 80% to about 125% of about 368 ng/mL.

In certain embodiments of the intravenous dosing regimens of the invention, the intravenous dosing regimen provides a Cmax of the M1 metabolite of tramadol at steady-state which is 48.3 ng/ml±12.3, or which is from about 80% to about 125% of about 48.3 ng/mL (i.e., from about 80 ng/ml to about 125 ng/ml). In certain embodiments of the intravenous dosing regimens of the invention, the intravenous dosing regimen provides an $AUC_{0-24}$ of the M1 metabolite of tramadol which is about 1001 ng·h/ml±257.5, or from about 80% to about 125% of about 1001 ng·h/ml.

In preferred embodiments of the intravenous dosing regimens of the invention, each dose of tramadol is administered intravenously over a time period from about 10 minutes to about 20 minutes. In certain preferred embodiments, each dose of the tramadol is administered over a time interval of 15 (±2) minutes.

In certain preferred embodiments of the intravenous dosing regimens of the invention, the method further comprises administering a first dose of tramadol to the patient intra-operatively at wound closure, or from first demand of analgesia post-operatively, and administering said further doses of intravenous tramadol for at least two days post-surgery.

In certain preferred embodiments of the intravenous dosing regimens of the invention, the method further comprises administering one or more doses of an intravenous opioid analgesic as rescue medicine to the patient to treat breakthrough pain.

In certain preferred embodiments of the intravenous dosing regimens of the invention, the method further comprises administering the first dose of tramadol on first demand of analgesia post-operatively, further comprising administering a therapeutically effective dose intravenous opioid analgesic to the patient at the end of the surgery.

In certain preferred embodiments of the intravenous dosing regimens of the invention, the method further comprises administering the first dose of tramadol to the patient intra-operatively at wound closure, further comprising administering a bolus of a therapeutically effective dose of intravenous opioid analgesic to the patient if the patient requests analgesia before the second dose of tramadol.

In certain preferred embodiments of the intravenous dosing regimens of the invention, the method further comprises administering a rescue opioid analgesic using Patient Controlled Analgesia (PCA).

In certain preferred embodiments of the intravenous dosing regimens of the invention, the treatment of pain in the patient is opioid-sparing over the first 48 hours post-surgery.

In certain preferred embodiments of the intravenous dosing regimens of the invention, the method further comprises diluting tramadol in a volume of normal saline to provide a unit dose (e.g., of about 25 mg tramadol) in said volume of normal saline; administering the dose of tramadol intravenously over a time period from about 10 to about 20 minutes, preferably about 15 (±2) minutes.

In certain preferred embodiments of the intravenous dosing regimens of the invention, the dose prior to dilution is contained in one or more ampoules.

In certain preferred embodiments of the intravenous dosing regimens of the invention, the ampoules contain tramadol hydrochloride and a buffering agent in water for injection.

In certain embodiments of the intravenous dosing regimens of the invention, the human patient(s) is suffering from acute post-operative pain.

In certain preferred embodiments of the intravenous dosing regimens of the invention, the method provides a reduction in at least one side-effect associated with tramadol therapy (e.g., as compared to prior art intravenous dosing regimens), wherein the side-effect is nausea, vomiting, or seizure.

In certain preferred embodiments of the intravenous dosing regimens of the invention, the method further comprises administering a therapeutically effective dose of an intravenous opioid analgesic is administered to the patient (i) at the end of the surgery, (ii) if the patient requests analgesia before the second dose of tramadol, or (iii) both (i) and (ii).

In certain preferred embodiments, the present invention is directed in part to a method of treating pain, comprising administering to a human patient(s) a therapeutically effective dose of tramadol intravenously over a time period from about 9, 10, 11, 12, 13, 14, 15, 16, 17, 18, 19, 20 21, 22, 23, 24, 25, 26, 27, 28, 29 30, 31, 32, 33, 34, 35, 36, 37, 38, 39, 40, 41, 42, 43, 44 or 45 minutes.

Further aspects of the invention are directed to diluting the dose of tramadol in from about 50 ml to about 500 ml (and preferably from about 50 ml to about 100 ml) of a pharmaceutically acceptable fluid for injection such as normal saline, e.g., in a bag, and standardizing the administration of the injection of the dose of tramadol via the use of a pump.

In another preferred embodiment, the dose of tramadol is provided in the form of a sterile solution at a concentration of about 12.5 mg to about 25 mg, or up to about 50 mg or 100 mg tramadol hydrochloride/1 ml prior to dilution.

In certain further preferred embodiments, the dose of tramadol prior to dilution is contained in one or more ampoules. In certain preferred embodiments, the ampoules contain the dose of tramadol (e.g., tramadol hydrochloride) together with a buffering agent (e.g., sodium acetate) in water for injection (e.g., about 1 ml to about 5 ml).

In certain further preferred embodiments, the method further comprises diluting the dose of tramadol into an IV bag for administration to the patient.

In certain preferred embodiments of the present invention, the method further comprises administering a first dose of tramadol to the patient intra-operatively at wound closure, or from first demand of analgesia postoperatively, and administering said further doses of intravenous tramadol for at least two days post-surgery.

In certain preferred embodiments of the present invention, the method further comprises the concomitant administration of one or more opioid analgesics, preferably via the injectable (e.g., intravenous) route as rescue medicine to the patient to treat breakthrough pain that the patient experiences, e.g., for the time period of at least about 48 hours post-surgery. Several options are available for postoperative pain management (Singelyn et al., 1998; Sinatra et al., 2002; both of which are hereby incorporated by reference). Options include intermittent "on-demand" analgesia, continuous epidural analgesia with opioids and/or local anesthetics is effective, or to provide a combination of nerve blocks with long-acting local anesthetics and/or opioids initiated intra-operatively and continued into the immediate postoperative period. For example, most Total knee Arthroplasty (TKA) or Total Hip Arthroplasty (THA) procedures are currently performed with regional (or neuraxial) or other nerve blocks and without general anesthesia. In certain preferred embodiments of the invention, the method further comprises administering a rescue opioid analgesic using Patient Controlled Analgesia (PCA). In certain preferred embodiments, the intravenous administration of opioid analgesic also or alternatively comprises opioid analgesic (e.g., morphine) intravenously to the patient at an effective dose (e.g., morphine in an amount of about 0.05 mg/kg) as a bolus at the end of surgery or upon first demand of analgesia postoperatively, to provide effective analgesia to the patient(s).

In certain preferred embodiments of the invention, the first dose of tramadol is administered on first demand of analgesia postoperatively. Thereafter, the method may further comprise administering a therapeutically (analgesically) effective dose intravenous opioid analgesic to the patient at the end of the surgery, to provide effective analgesia to the patient(s).

In certain preferred embodiments of the invention, the first dose of tramadol is administered to the patient intra-operatively at wound closure. In such embodiments, the method may further comprise administering a bolus of a therapeutically (analgesically) effective dose of intravenous opioid analgesic to the patient if the patient requests analgesia before the second dose of tramadol, to provide effective analgesia to the patient(s).

In preferred embodiments where the tramadol is administered for the treatment of post-operative pain, the treatment of pain in the patient is opioid-sparing over the first 48 hours post-surgery.

In other preferred embodiments, the human patient(s) suffering from pain is unable to ingest an oral dosage form (e.g., of tramadol or another opioid analgesic and/or an NSAID) because the patient is suffering from cancer pain.

In accordance with the above, the final drug product (containing the intravenous dose of tramadol) may be presented as, e.g., as unit-dose ampoules, unit-dose vials, multi-dose ampoules, multi-dose vials, and drug in pre-mixed bags.

In certain preferred embodiments, the M1 metabolite of tramadol (0-desmethyltramadol) contributes to analgesic effect provided by the present invention (dosing regimen), without being toxic (e.g., without significant side effects) to humans at the administered dose of intravenous tramadol.

In certain preferred embodiments, the present methods are used to treat human patient(s) suffering from acute post-operative pain. In further embodiments, the method may result in a reduction in at least one side-effect associated with tramadol therapy, wherein the side-effect is nausea, vomiting, or seizure. In certain preferred embodiments, a therapeutically effective dose of an intravenous opioid analgesic is administered to the patient (i) at the end of the surgery, (ii) if the patient requests analgesia before the second dose of tramadol, or (iii) both (i) and (ii). In certain preferred embodiments, each dose of tramadol is administered intravenously over a time period from about 10 minutes to about 20 minutes, or each dose of tramadol is administered over a time interval of 15 (±2) minutes. In certain preferred embodiments, the pharmacokinetic profile (e.g., plasma concentration curve of tramadol and/or the M1 metabolite of tramadol) achieved with the (e.g., about) 25 mg dosing regimen provides surprisingly reduced fluctuation (e.g., peak to trough variance) as compared to a higher (e.g., 75 mg or 100 mg) intravenous dosing regimen. In certain preferred embodiments, the pharmacokinetic profile (e.g., Cmax and AUC) achieved by this IV tramadol dosing regimen at a time where the patient might be switched to oral meds (e.g., after the 44-48 hour dosing interval) is similar to the pharmacokinetic profile (e.g., Cmax and AUC) provided at steady-state by a dosing regimen of 100 50 mg tramadol HCl administered orally every 6 hours. This allows the patient to be stepped down from the intravenous tramadol dosing regimen to an oral dosing regimen. In turn, this allows the patient to be discharged from hospital care with less concern about deleterious effects which might occur from a switch from intravenous to oral analgesic medicine (e.g., the switch to an oral version of the drug providing a much different Cmax and AUC).

In certain preferred embodiments, the present methods are used to treat human patient(s) suffering from acute post-operative pain. In further embodiments, the method may result in a reduction in at least one side-effect associated with tramadol therapy, wherein the side-effect is nausea, vomiting, or seizure. In certain preferred embodiments, a therapeutically effective dose of an intravenous opioid analgesic is administered to the patient (i) at the end of the surgery, (ii) if the patient requests analgesia before the second dose of tramadol, or (iii) both (i) and (ii). In certain preferred embodiments, each dose of tramadol is administered intravenously over a time period from about 10 minutes to about 20 minutes, or each dose of tramadol is administered over a time interval of 15 (±2) minutes. In certain preferred embodiments, the pharmacokinetic profile (e.g., plasma concentration curve of tramadol and/or the M1 metabolite of tramadol) achieved with the (e.g., about) 25 mg dosing regimen provides surprisingly reduced fluctuation (e.g., peak to trough variance) as compared to a higher (e.g., 75 mg or 100 mg) intravenous dosing regimen. In certain preferred embodiments, the pharmacokinetic profile (e.g., Cmax and AUC) achieved by this IV tramadol dosing regimen at a time where the patient might be switched to oral meds (e.g., after the 44-48 hour dosing interval) is similar to the pharmacokinetic profile (e.g., Cmax and AUC) provided at steady-state by a dosing regimen of 100 mg tramadol HCl administered orally every 6 hours. This allows the patient to be stepped down from the intravenous tramadol dosing regimen to an oral dosing regimen. In turn, this allows the patient to be discharged from hospital care with less concern about deleterious effects which might occur from a switch from intravenous to oral analgesic medicine (e.g., the switch to an oral version of the drug providing a much different Cmax and AUC).

The methods of the present invention are described in further detail in the following sections. However, it should be understood that for purposes of the present invention, the following terms have the following meanings:

For purposes of the present invention, the phrase "from about 25 mg to less than 50 mg" means that the dose of intravenous tramadol may be, e.g., 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, and 49.5 mg.

With respect to the second dose of intravenous tramadol administered to the human patient in this method, for purposes of the present invention the term "about 50 mg" means, e.g., from about 45 mg to about 55 mg, or 45 mg, 46 mg, 47 mg, 48 mg, 49 mg, 50 mg, 51 mg, 52 mg, 53 mg, 54 mg, and 55 mg.

For purposes of the present invention, the term "less than 50 mg" means, e.g., that the dose of intravenous tramadol may be 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, and 49.5 mg.

The term "acute pain" as used herein means pain that has a sudden onset and commonly declines over a short time (days, hours, minutes) and follows injury to the body and which generally disappears when the bodily injury heals.

The term "effective analgesia" is defined for purposes of the present invention as a satisfactory reduction in or elimination of pain, along with the process of a tolerable level of side effects, as determined by the human patient.

The term "effective pain management" means for purposes of the present invention as the objective evaluation of a human patient's response (pain expressed versus side effects) to analgesic treatment by a physician as well as subjective evaluation of therapeutic treatment by the patient undergoing such treatment. The skilled artisan will understand that effective analgesia will vary according to many factors, including individual patient variations.

The term "breakthrough pain" means pain which the patient experiences despite the fact that the patient is being administered generally effective amounts of, e.g., an opioid analgesic such as buprenorphine.

The term "rescue" refers to a dose of an analgesic which is administered to a patient experiencing breakthrough pain.

An "effective amount" is an amount sufficient to effect beneficial or desired clinical results including alleviation or reduction in pain. In some embodiments, the "effective amount" may reduce the pain of ongoing pain and/or break-through pain (including ambulatory pain and touch-evoked pain).

The term "parenterally" as used herein includes subcutaneous injections, intravenous, intramuscular, intrasternal injection or infusion techniques.

The term "patient" as used herein refers to a warm blooded animal such as a mammal which is the subject of trauma, e.g., surgical trauma. It is understood that at least humans, dogs, cats, and mice are within the scope of the meaning of the term.

As used herein, the term "treat" or "treatment", or a derivative thereof, contemplates partial or complete inhibition of acute pain, when a composition of the present invention is administered following the onset of acute pain.

DETAILED DESCRIPTION

Figure 1:
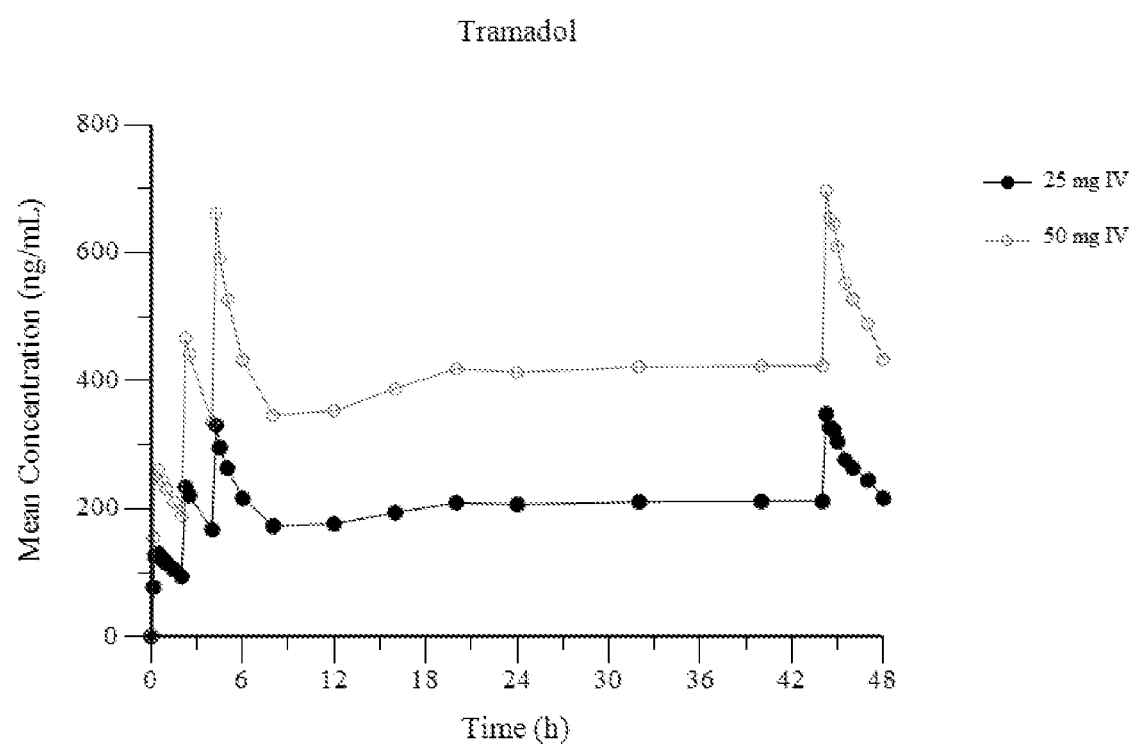
FIG. 1 is a graph showing a mean plasma concentration-time profile (linear scale) for intravenous tramadol administered at a dose of 25 mg as per Example 2.

The chemical name for tramadol is (±)cis-2-[(dimethyl-amino)methyl]-1-(3-methoxyphenyl) cyclohexanol hydrochloride [or (1R,2R)-rel-2-[(dimethyl-amino)methyl]-1-(3-methoxyphenyl) cyclohexanol hydrochloride, (1RS,2RS)-2-[(dimethylamino)methyl]-1-(3-methoxyphenyl) cyclohexanol hydrochloride, (±)-(RR, SS)-2-[(dimethyl-amino)methyl]-1-(3-methoxyphenyl) cyclohexanol hydrochloride]. Unless otherwise specified, the term tramadol refers to the racemic mixture of the (±)cis isomers.

Tramadol is a centrally-acting synthetic analgesic of the aminocyclohexanol group with opioid-like effects. Tramadol is extensively metabolized following administration resulting in a number of enantiomeric metabolites which display different opioid-receptor binding properties, and monoaminergic reuptake inhibition (Grond and Sablotzki, 2004). Both enantiomers of tramadol and (+)-M1 are responsible for the analgesic effect. The primary metabolite [(+)-M1 or (+)-O-desmethyltramadol] of tramadol confers significant μ-opioid activity; (+)-tramadol confers weak μ-opioid activity and significant serotonin reuptake inhibition; and (−)-tramadol is responsible for the inhibition of noradrenaline re-uptake (Gillen et al., 2000; Raffa, 2008). Nonclinical studies have shown that antinociception induced by tramadol is only partially antagonized by the opiate antagonist, naloxone, indicating that non-opioid mechanisms are also involved in its pharmacodynamic action (Collart et al., 1992).

Tramadol has efficacy in management of acute postoperative pain equivalent to morphine and other opioids administered intravenously, although the onset of action for tramadol is slower. The parenteral route has the advantage of immediate bioavailability and faster onset of action than oral, and is available to postoperative patients who cannot take oral medications. Current standard-of-care injectable analgesics (opioids and NSAIDs) have significant adverse effects, including opiate-induced respiratory depression, excessive sedation, hypotension, dependency, increased bleeding risk, renal toxicity and gastrointestinal irritation, which can potentially slow the postoperative rehabilitation process and compound the risk inherent in any surgical procedure.

Tramadol is currently commercially available in various countries/territories in the following forms: 50 mg/ml or 100 mg/2 ml, solution for injection; 50 mg, capsules, hard; 50 mg, prolonged-release tablets; 100 mg, prolonged-release tablets; 150 mg, prolonged-release tablets; 200 mg, prolonged-release tablets; 50 mg, tablets; 100 mg/ml, oral drops, solution; and 100 mg, suppositories. In the U.S., tramadol is approved by the Food and Drug Administration (FDA) and marketed as an oral capsule/tablet for moderate to moderately severe pain in adults, e.g., under the tradename Ultram® (tramadol hydrochloride tablets).

Parenteral tramadol has been used extensively in Europe and other areas of the world for the amelioration of postoperative pain in both adults and children. The efficacy of tramadol has been thoroughly reviewed (Lee C R, McTavish D, Sorkin E M. Tramadol. A preliminary review of its pharmacodynamic and pharmacokinetic properties, and therapeutic potential in acute and chronic pain states. Drugs. 1993; 46:313-340; Scott L J, Perry C M. Tramadol. A review of its use in perioperative pain. Drugs. 2000; 60:139-176; Grond S and Slabotzi A. Clinical pharmacology of tramadol. Clin Pharmacokinet. 2004; 43:879-923). Parenteral tramadol in such territories consists of tramadol 50 mg or 100 mg administered as a slow bolus injection (over 2-3 minutes) every 4-6 hours. Despite the availability of parenteral (e.g., intravenous) and oral forms of tramadol, Applicant is not aware of any established dosing regimen of parenteral (e.g., intravenous) tramadol in a dose of less than 50 mg, e.g., 25 mg for adult human patients. However, at page 6 of the product label for Ultram® in the U.S., it is reported that a 16-day titration schedule, starting with 25 mg qAM and using additional doses in 25 mg increments every third day to 100 mg/day (25 mg four times per day), followed by 50 mg increments in the total daily dose every third day to 200 mg/day (50 mg four times per day), resulted in fewer discontinuations due to nausea or vomiting and fewer discontinuations due to any cause than did a 10-day titration schedule. However, this dosage regimen is for chronic pain with oral tramadol.

The product label for Ultram® further states that for patients with moderate to moderately severe chronic pain not requiring rapid onset of analgesic effect, the tolerability of ULTRAM® can be improved by initiating therapy with the following titration regimen: ULTRAM® should be started at 25 mg/day qAM and titrated in 25 mg increments as separate doses every 3 days to reach 100 mg/day (25 mg q.i.d.). Thereafter the total daily dose may be increased by 50 mg as tolerated every 3 days to reach 200 mg/day (50 mg q.i.d.). After titration, ULTRAM® 50 to 100 mg can be administered as needed for pain relief every 4 to 6 hours not to exceed 400 mg/day. (page 20-21 of the package insert for ULTRAM®).

Surgical procedures often result in some form of acute pain. Surgical pain may include nociceptive, neuropathic or psychological components. Nociceptive pain is a pain experienced as a result of nociception, which is detection of a stimulus by a pain receptor (nociceptor) and transmission of the information to the brain along nerves. Nociceptive pain is caused by tissue damage and inflammation in response to trauma. The resulting pain is usually not well localized and is opioid responsive.

Several options are available for postoperative pain management (Singelyn et al., 1998; Sinatra et al., 2002). Options include intermittent "on-demand" analgesia, continuous epidural analgesia with opioids and/or local anesthetics is effective, or to provide a combination of nerve blocks with long-acting local anesthetics and/or opioids initiated intraoperatively and continued into the immediate postoperative period. In the United States (US) and in India, this latter strategy is frequently employed, and most TKA and THA procedures are currently performed with regional (or neuraxial) or other nerve blocks and without general anesthesia. Each of these options for postoperative pain management can be used concomitantly with the intravenous tramadol treatments described herein as rescue medicine to treat breakthrough pain.

The present invention is directed in part to tramadol in a pharmaceutically acceptable sterile solution formulation containing an effective dose of tramadol or a pharmaceutically acceptable salt thereof, and a method of administration of the same for the treatment of pain, e.g., postoperatively. Tramadol injection in accordance with the present invention will fulfill an important need by providing a safe and effective alternative injectable analgesic for use in the acute postoperative setting.

Preferably, the dose of tramadol administered in accordance with the present invention is, e.g., about 25 mg. In certain preferred embodiments, each tramadol dose administered is in the amount of, e.g., 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg, e.g., provided as tramadol hydrochloride. The tramadol may be provided, e.g., as 25 or 50 mg tramadol hydrochloride/1 ml. The injectable tramadol dose is generally intended for in-hospital use, although it can be used in other settings. In certain preferred embodiments, the therapeutically effective dose of tramadol intravenously over a time period from about 10 minutes to about 20 minutes, and most preferably in certain embodiments about 15 (±2) minutes. Thus, in preferred embodiments, the therapeutically effective dose of tramadol intravenously over a time period from about 9, 10, 11, 12, 13, 14, 15, 16, 17, 18, 19, or 20 minutes.

Further aspects of the invention are directed to diluting the dose of tramadol in from about 50 ml to about 100 ml of a pharmaceutically acceptable fluid for injection (such as normal saline), and standardizing the administration of the injection of the dose of tramadol via the use of a pump. In preferred embodiments, the pump is an infusion pump that is commercially available, such as pumps available from Braun and Hospira.

As previously mentioned, the dose of tramadol administered in accordance with the present invention may be diluted in a suitable pharmaceutically acceptable carrier for injection. Examples of such include sterile water for injection, normal saline, etc. Intravenous fluids are well known to those of ordinary skill in the art, and may include other ingredients beyond the dose of tramadol and the carrier/solvent for the tramadol, e.g., sterile solutions of simple chemicals such as sugars, amino acids or electrolytes, which can be easily carried by the circulatory system and assimilated. Such fluids are typically prepared with water for injection USP. Fluids used commonly for intravenous (IV) use are disclosed in Remington, The Science and Practice of Pharmacy [full citation previously provided], and include: alcohol, e.g., 5% alcohol (e.g., in dextrose and water ("D/W") or D/W in normal saline solution ("NSS"), including in 5% dextrose and water ("D5/W"), or D5/W in NSS); synthetic amino acid such as Aminosyn, FreAmine, Travasol, e.g., 3.5 or 7; 8.5; 3.5, 5.5 or 8.5% respectively; ammonium chloride e.g., 2.14%; dextran 40, in NSS e.g., 10% or in D5/W e.g., 10%; dextran 70, in NSS e.g., 6% or in D5/W e.g., 6%; dextrose (glucose, D5/W) e.g., 2.5-50%; dextrose and sodium chloride e.g., 5-20% dextrose and 0.22-0.9% NaCl; lactated Ringer's (Hartmann's) e.g., NaCl 0.6%, KCl 0.03%, $CaCl_2$) 0.02%; lactate 0.3%; mannitol e.g., 5%, optionally in combination with dextrose e.g., 10% or NaCl e.g., 15 or 20%; multiple electrolyte solutions with varying combinations of electrolytes, dextrose, fructose, invert sugar Ringer's e.g., NaCl 0.86%, KCl 0.03%, $CaCl_2$) 0.033%; sodium bicarbonate e.g., 5%; sodium chloride e.g., 0.45, 0.9, 3, or 5%; sodium lactate e.g., ⅙ M; and sterile water for injection The pH of such IV fluids may vary, and will typically be from about 3.5 to about 8 as known in the art.

The dose of tramadol or pharmaceutically acceptable salts thereof can be administered alone or in combination with other medical treatments, or other therapeutic agents, such as NSAIDs. When so-used, other therapeutic agents can be administered before, concurrently (whether in separate dosage forms or in a combined dosage form), or after administration of an active agent of the present invention.

Consistent with the known clinical effects of opioids, nonclinical safety pharmacology studies have shown that tramadol at high doses affects the central nervous system (CNS), producing sedation, impaired mobility, vomiting (dogs), decreased activity, and convulsions (Matthiesen et al., 1998). Also consistent with clinical effects, changes in blood pressure have been observed in cardiovascular studies in rats at high doses (Raimundo et al., 2006). Tramadol use, particularly with high doses, has been associated with seizures, and the risk of seizures is increased in the presence of drugs that reduce seizure threshold, head trauma or prior history of seizures.

The toxicity of tramadol has been summarized by Matthiesen, et al. (1998). The single-dose toxicity of tramadol was similar in all species tested, independent of the route of administration. Notable acute findings included restlessness, unsteady gait, reduced spontaneous activity, exophthalmus, mydriasis, salivation, vomiting (dog), tremor, convulsions, slight cyanosis and dyspnea. The principle findings in repeat-dose toxicity studies in rats and dogs were behavioral/clinical signs and convulsions at doses of >25 mg/kg/day. The kidney and liver were identified as potential target organs in rats, with mild effects (minimal tubular vacuolization and perivenular hydropic degeneration, respectively) following repeat intraperitoneal dosing at high doses of tramadol.

There was no evidence of genotoxic potential for tramadol in standard in vitro and in vivo studies (Matthiesen et al., 1998). Carcinogenicity bioassays in mice and rats showed no evidence of carcinogenic potential. An extensive reproductive and teratology program revealed no safety concerns with respect to fertility or teratogenic effects after oral administration (Matthiesen et al., 1998; Yamamoto et al., 1972). Toxicity to offspring only occurred at doses associated with maternal toxicity.

Following oral administration, tramadol is rapidly and almost completely absorbed. The pharmacokinetics of tramadol were evaluated in healthy male volunteers (n=10) in a crossover design using 100 mg PO or IV doses (Lintz et al., 1986). Peak serum concentrations (tmax) were reached approximately 2 hours after oral dosing and the peak serum concentration (Cmax) for PO tramadol was 280±49 ng/mL. The terminal half-life was 5.1 hours for PO and 5.2 hours for IV administration. The area under the serum tramadol concentration-time curve (AUC) was 2488±774 ng·h/mL for PO and 3709±977 ng·h/mL for IV administration. Total clearance was 467±124 mL/min for PO and 710±174 mL/min for IV administration. The absolute bioavailability of the oral dose was 68±13%, based on comparison of the AUC values, while the estimated absorption of the oral dose was 86-88%. The difference between absorption and bioavailability was attributed to first pass metabolism, which was estimated to be ~20%. However, the absolute bioavailability approaches 90-100% with continuous dosing, probably due to saturation of first pass metabolism (Liao et al., 1992). Other studies have corroborated these findings (Grond and Sablotzki, 2004).

The pharmacokinetic profile of tramadol following i.v. and p.o. administration in humans (n=10, male) is summarized in Table A below (Lintz W, Barth H, Osterloh O, Schmidt-Bothelt E. Bioavailability of enteral tramadol formulations. 1st communication: capsules. Arzneim Forsch Drug Res. 1986; 36:1278-1283). The absolute oral bioavailability of tramadol was 68% (±13) in humans.

TABLE A

Pharmacokinetics of Tramadol (100 mg) Following Intravenous and Oral Administration to Humans

| Tramadol (100 mg) | $C_{max}$ (ng/mL) | $t_{1/2}$ (h) | $AUC_{0-24\,h}$ (ng · h/mL) | $V_d$ (L) | CL/F (mL/min) |
|---|---|---|---|---|---|
| i.v. | — | 5.2 ± 0.8 | 3709 ± 977 | 203 ± 40 | 467 ± 124 |
| p.o | 280 ± 49 | 5.1 ± 0.8 | 2488 ± 774 | 306 ± 52 | 710 ± 174 |

Abbreviations:
$C_{max}$, maximal concentration;
$t_{1/2}$, half-life;
AUC, area under the plasma concentration-time curve;
CL, clearance;
F, bioavailability;
$V_d$, volume of distribution The pharmacokinetic profile of tramadol and the (+)-M1 and (−)-M1 metabolites was also evaluated in humans (N=12, male) following p.o. administration of a single 1.5 mg/kg dose of tramadol (Matthiesen, et al., 1993). The data are summarized in Table B below:

TABLE B

Pharmacokinetics of Tramadol and the (+) and (−) Enantiomers of the M1 Metabolite

| Tramadol (1.5 mg/ kg, [100 mg]) | $C_{max}$ (ng/mL) | $T_{max}$ (h) | $t_{1/2}$ (h) | AUC (ng · h/mL) | CL/F (mL/ min/kg) |
|---|---|---|---|---|---|
| Tramadol | 274 ± 75 | 1.6 ± 0.5 | 5.9 ± 0.7 | 2177 ± 722 | 742 ± 234 |
| (+)-M1 | 147 ± 39 | 1.6 ± 0.5 | 6.0 ± 1.0 | 1258 ± 410 | 642 ± 204 |
| (−)-M1 | 125 ± 32 | 1.5 ± 0.5 | 5.2 ± 0.8 | 908 ± 298 | 883 ± 264 |

Abbreviations:
$C_{max}$, maximal concentration;
$T_{max}$, time to maximal concentration;
AUC, area under the plasma concentration-time curve;
CL, clearance;
F, bioavailability;
$t_{1/2}$, half-life;
$V_d$; volume of distribution Tramadol undergoes hepatic metabolism and both the parent drug and the active metabolite are excreted by the kidneys. The active metabolite, M1 (0 desmethyltramadol), is produced by the action of CYP2D6 isozyme of the cytochrome P450 enzyme system. It has a half-life of approximately 6.7 hours after oral administration (single dose of 100 mg), compared to a half-life of 5.6 hours for tramadol administered intravenously. Hepatic impairment results in decreased metabolism of both the parent compound and the active metabolite. Tramadol is rapidly distributed after IV administration with a distribution half-life in the initial phase of 0.31±0.17 hours, followed by a slower distribution phase with a half-life of 1.7±0.4 hours (Lintz et al., 1986). The volumes of distribution following PO and IV administration were 306 L and 203 L, respectively, indicating that tramadol has a high tissue affinity. The protein binding of tramadol is approximately 20%; however, saturation of binding sites does not occur in the therapeutic dose range (Ultram® Prescribing Information, 2009).

Elimination half-life increases approximately 2-fold in subjects with renal or hepatic impairment. Patients who metabolize drugs poorly via CYP2D6 (Caucasian population prevalence ~8%) may obtain reduced benefit from tramadol due to reduced formation of M1 (Ultram® Prescribing Information, Ortho-McNeil-Janssen Pharmaceuticals, Inc, 2009).

Studies of IV tramadol in the postoperative setting have shown an acceptable safety profile. Loading doses up to 150 mg IV were not associated with any serious adverse effects (Silvasti et al., 2000). Also, no serious adverse effects were observed in clinical trials of tramadol with mean (±SD) cumulative doses of 449±66 mg (Rud et al., 1994), 677±473 mg (range 128-1750 mg) (Silvasti et al., 2000), and 868.3±412.2 mg (Pang et al., 1999) over 24, 36 and 48 h respectively.

The most common adverse events, nausea, dizziness, headache, somnolence, sweating, fatigue, constipation, dry mouth and vomiting, which are usually mild to moderate in severity and only occasionally lead to premature discontinuation of tramadol.

The Ultram® and Tramal® labels contain several warnings and precautions regarding use of tramadol. The risk of most of these potential adverse events can be minimized by decreasing the dose or excluding use of tramadol in subjects with risk factors associated with these known, rare adverse events. Tramadol metabolism is reduced in the setting of advanced cirrhosis and renal clearance of both tramadol and its metabolites is reduced in individuals with creatinine <30 mL/min. Thus, the dose of tramadol should be reduced by half or the interval doubled in these populations. Dosage adjustment is also recommended in individuals >75 years of age as they have reduced drug clearance. Tramadol is metabolized by CYP2D6 and CYP3A4; thus, drugs that are inhibitors or inducers of these enzymes can alter tramadol metabolism, resulting in decreased efficacy and/or increased risk of seizures or other adverse effects. Tramadol is associated with a low risk for respiratory depression, which is increased in the presence of other opioids, anesthetic agents and other CNS depressants, including alcohol. Respiratory depression due to the opioid activity of tramadol can be reversed with naloxone. Naloxone should be used cautiously as it can potentiate seizures when administered with tramadol. The full range of allergic/hypersensitivity reactions have been reported in association with tramadol administration, including serious and rarely fatal anaphylactoid reactions.

Potentially life-threatening serotonin syndrome may occur with tramadol products with concomitant use of serotonergic drugs such as SSRIs, tricyclic antidepressants, monoamine oxidase inhibitors and triptans.

Tramadol use, particularly with high doses, has been associated with seizures, and the risk of seizures is increased in the presence of drugs that reduce seizure threshold, head trauma or prior history of seizures.

Human studies evaluating the abuse potential of tramadol, administered via IV or PO routes, have also been conducted (Epstein et al., 2006). During the initial dose-ranging studies, seizure was observed following a tramadol dose of 700 mg IV administered over 1 minute and 300 mg IV delivered over 2.5 minutes. No seizures were observed with a tramadol dose of 200 mg IV administered over 5 minutes. The authors hypothesized that toxicity is likely to limit abuse of high doses of IV tramadol. In a subsequent study involving 10 experienced opioid abusers, tramadol (100 and 200 mg IV), morphine (10 and 20 mg IV) and placebo were administered over 5 minutes. The endpoints in the study were subjective; the extent to which subjects "liked" the effects of the drugs, as well as their ability to produce effects common to morphine and benzadrine (assessed by the Addiction Research Center Inventory-Morphine Benzadrine Group [ARCI-MBG] scale). Tramadol and morphine significantly increased ratings of "feel drug effect" compared to placebo. However, neither dose of tramadol increased ratings on the "liking" or ARCI-MBG scale or on any other subjective measure of opiate-like effects. In contrast, morphine 10 and 20 mg doses significantly increased ratings of "liking" and the morphine 20 mg dose increased ratings on the ARCI-MBG scale. Thus, tramadol administered via the parenteral route (IV or IM) is unlikely to be associated with the subjective morphine-like and positive mood effects typical of abuse and addiction.

In accordance with the present invention, it is desirable to provide an intravenous dosing regimen of tramadol which at steady-state provides a plasma concentration with respect to Cmax and AUC that is similar or equivalent to the steady-state Cmax and AUC provided by a 100 mg oral tramadol dose given every 6 hours would be desirable and would be safer and have less likelihood of significant side effects than, e.g., the administration of 50 or 100 mg of tramadol intravenously administered every 6 hours (i.e., same dose and dosing interval as the oral reference standard, Ultram®. It is further believed that it would desirable for such an intravenous dosing regimen(s) to provide a steady-state trough plasma level of tramadol (e.g., Cmin) which is at least as high as the steady-state trough level provided by a 100 50 mg oral tramadol dose given every 6 hours. It is further desirable in accordance with the present invention to provide a dosing regimen which reaches but does not substantially exceed the maximum (Cmax) and minimum (Cmin) plasma levels of tramadol obtained at steady-state by a 100 50 mg oral tramadol dose given every 6 hours as soon as possible within the dosing regimen, e.g., prior to the end of the initial 24 hours of intravenous tramadol, or sooner. As will be explained further herein, for purposes of the present invention the steady-state Cmax of the 50 mg oral dose of tramadol administered every 6 hours is about 368 ng/mL. For purposes of the present invention, a similar or equivalent Cmax provided by an intravenous tramadol dosing regimen would provide a Cmax within the range from about 80% to about 125% of the steady-state Cmax and/or Cmin of the 50 mg oral tramadol administered every 6 hours. It is especially preferred that the steady-state Cmax of the dosing regimen(s) of the present invention does not exceed the concentration provided by 50 mg oral tramadol administered every 6 hours, at steady-state by more than 15% or more than about 10% (of this range)

In accordance with the present invention, the intravenous tramadol dosing regimens of the present invention and as described herein will be similar to, not significantly less than, match or exceed the analgesic efficacy of a 50 mg immediate release oral tramadol dose given every 6 hours, but may reduce side effects and/or may improve tolerance as compared to that oral formulation.

The above goals and others are achieved by the present invention, wherein the dose of tramadol is reduced relative to the approved oral dose (50 mg) in the U.S., with the addition of at least one loading dose administered in a shortened dosing interval as compared to the reference standard (Ultram® 50 mg oral tablets). By decreasing the dose of tramadol but increasing the number of administrations during the initial 24 hour period of tramadol administration, the present invention achieves the goal of a lowered dose providing similar Cmax, AUC and efficacy as compared to the orally administered 50 mg tramadol Q6h.

In a preferred embodiment, the dosing regimen comprises 25 mg IV tramadol at hour 0, followed by 25 mg at hour 2, 25 mg at hour 4, and 25 mg every 4 hours thereafter (e.g., until the patient no longer requires treatment with intravenous tramadol). In this embodiment, the maximum plasma concentration (Cmax) of the tramadol rapidly approaches (e.g., at about 4 hours after the initial intravenous dose, or, e.g., after the third intravenous dose) the maximum concentration found at steady-state with respect to a dosing regimen of 50 mg tramadol HCl administered orally every 6 hours (which steady-state does not occur until about 44 hours after the initial oral dose).

The intravenous tramadol formulation in accordance with the invention typically includes tramadol in the form of its hydrochloride salt. However, one of ordinary skill in the art will appreciate that other forms of tramadol may be used, including but not limited to all pharmaceutically acceptable salts of tramadol. Such pharmaceutically acceptable salts may include, but are not limited to, metal salts such as sodium salt, potassium salt, secium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate, and the like; amino acid salts such as arginate, asparginate, glutamate and the like.

It is contemplated that with respect to the inventive methods for the intravenous administration of tramadol as described herein, other analgesics, preferably opioid analgesics, may be used to treat postoperative pain in the patient(s), as well. It is particularly contemplated that one or more opioid analgesics will be administered post-surgically to the patient as rescue medicine in order to treat breakthrough pain that the patient may experience.

The term "opioid analgesic" refers to all drugs, natural or synthetic, with morphine-like actions. The synthetic and semi-synthetic opioid analgesics are derivatives of five chemical classes of compound: phenanthrenes; phenylheptylamines; phenylpiperidines; morphinans; and benzomorphans, all of which are within the scope of the term. Opioid analgesics which are useful in the present invention include all opioid agonists or mixed agonist-antagonists, partial agonists, including but not limited to alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, mixtures of any of the foregoing, salts of any of the foregoing, and the like.

In certain preferred embodiments, opioid analgesics include morphine, oxycodone, codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine or pharmaceutically acceptable salts thereof. In certain preferred embodiments, the opioid agonist is morphine. Equianalgesic doses of these opioids are generally known to those persons having ordinary skill in the art.

In certain embodiments, the patient's need for additional analgesic treatment beyond the intravenous tramadol may be ascertained via the use of a surrogate measure of pain. Pain rating scales are used in daily clinical practice to measure pain intensity. The commonly used measurement scales include the Visual Analog Scale (VAS), the Graphic Rating Scale (GRS), the Simple Descriptor Scale (SDS), the Numerical Rating Scale (NRS), and the Faces Rating Scale (FRS). All of these scales have been documented as being valid measures of pain intensity. The three scales most commonly used in the U.S. are the numerical, word and faces scales. One preferred pain rating scale is the visual analog scale (VAS), a 10 cm. vertical or horizontal line with word anchors at the extremes, such as "no pain" on one end and "pain as bad as it could be" at the other. The patient is asked to make a mark along the line to represent pain intensity.

Alternatively, the graphic rating scale (GRS) is a variation of the visual scale which adds words or numbers between the extremes. Wording added might include "no pain", "mild", "severe". The descriptor scale (SDS) is a list of adjectives describing different levels of pain intensity. For example pain intensity may be described as "no pain", "mild", "moderate" or "severe". The numerical pain rating scale (NPRS) refers to a numerical rating of 0 to 10 or 0 to 5 or to a visual scale with both words and numbers. The patient is asked to rate the pain with 0 being no pain and 10 being the worst possible pain. The faces scale was developed for use with children. This scale exists in several variations but relies on a series of facial expressions to convey pain intensity. Grouping patients' rating of pain intensity as measured with a numerical scale ranging from 0 to 10 into categories of mild, moderate, and severe pain is useful for informing treatment decisions, and interpreting study outcomes. In 1995, Serlin and colleagues (Pain, 1995, 277-84) developed a technique to establish the cut points for mild, moderate, and severe pain by grading pain intensity and functional inference. Since then, a number of studies have been conducted to correlate the numerical scales, for example the NPRS, with cutpoints related to levels of pain intensity. Common severity cutpoints are (1 to 4) for mild pain, (5 to 6) for moderate pain, and (7 to 10) for severe pain.

Surrogate measures of opioid efficacy (analgesia) include sedation, respiratory rate and/or pupil size (via pupillometry), and visual analogue scale ("VAS") for "drug effect". The Sum of Pain Intensity Differences (SPID) through 48 hours post first dose (SP1D48) at rest may be used as a primary measure of efficacy.

The intravenous tramadol dosing regimens of the invention may be used in the in the hospital or day hospital setting and therefore administered by medical staff. The tramadol hydrochloride injection for intravenous use and its dosing regimen can fill an important need in addition to tramadol (e.g., ULTRAM®) tablets and tramadol (e.g., ULTRAM® ER) extended-release tablets by providing this safe and effective injectable analgesic with a novel mechanism of action (μ-opioid agonist and monoaminergic reuptake inhibition) for use in the acute post-operative setting. These dosing regimens may be used, e.g., for all types of surgery, including orthopedic surgery (e.g., total knee replacement, bunionectomy) or soft tissue surgery (e.g., elective abdominoplasty).

DETAILED DESCRIPTION OF PREFERRED EMBODIMENTS

This invention is further illustrated by the following examples that should not be construed as limiting. Those of skill in the art of pharmaceutical formulation will readily appreciate that certain modifications to the examples may be readily effected. Any methods, materials, or excipients which are not particularly described will be generally known and available those skilled in the drug design and assay and pharmacokinetic analysis.

Example 1

In Example 1, a pharmacokinetic (PK) study in healthy volunteers was conducted to evaluate the relative exposure of two intravenous (IV) dose regimens of tramadol compared to the approved 100 mg Q6h oral dose regimen of tramadol. The two tramadol IV dosing regimens were based on various pharmacokinetic (PK) simulations done prior to the study, and it was determined that the following were appropriate for evaluation: (1) 75 mg IV REGIMEN: IV tramadol 75 mg administered at Hour 0, followed by 75 mg at Hour 3 and Hour 6, and 75 mg every 6 hours thereafter through Hour 42; (2) 50 mg IV REGIMEN: IV tramadol 50 mg administered at Hour 0, followed by 50 mg at Hour 2, 50 mg at hour 4, and 50 mg every 4 hours thereafter through Hour 44. These two IV dosing regimens were studied in a multiple-dose, randomized, PK 3-way crossover study in 18 healthy volunteers, each of whom also received 100 mg oral tramadol given every 6 hours during one of the periods through Hour 42.

Examination of the parent (tramadol) as well as the primary metabolite (M1 0-desmethyltramadol) was performed over the 48-hour treatment period. A focus of the analysis was on assessment of Cmax values (to ensure the Cmax for the IV formulation was similar to that of the oral formulation) as well as on early concentrations during the first doses (to ensure adequate medication would be provided during the initial 6 to 12 hours of treatment as the drugs reached steady-state concentrations). Overall exposure to tramadol was estimated from average trough plasma concentrations.

A fitted curve was obtained because the second oral peak was not measured in the study. For the modeling portion of the analysis, a validated Phoenix® WinNonlin® program version 6.4 (Certara) was used for PK analysis, simulation, graphics, tables and statistical calculations. Tramadol plasma concentration-time data observed over the initial 24 hours was fit to a linear 1-compartment model with first-order absorption and a lag time. For purposes of nonlinear regression, the data were weighted as 1/observed. Predicted concentration-time data were calculated based on the individual fitted PK parameters. The oral Cmax and AUC values over the initial 12 and 24 hours after administration was calculated using noncompartmental analysis of the predicted concentration using a fitted model.

Mean plasma tramadol concentrations just after administration (for example at 3, 6, and 42 h) were higher after 75 mg IV q6h compared to the administration of 50 mg IV q4h and 100 mg PO q6h. As evidenced from the trough/pre-dose samples between 24 and 42 h, the mean tranomadol concentrations were very similar for 50 mg IV q4h and 100 mg PO q6h but somewhat lower for 75 mg IV q6h.

The mean tramadol concentrations for 50 mg IV q4h and 100 mg PO q6h were almost superimposable at the end of the pharmacokinetic sampling period, between approximately 44 and 48 h, suggesting that the two regimens provided similar steady-state concentrations (including trough and Cmax concentrations). The mean plasma O-desmethyltramadol concentrations were higher for 75 mg IV q6h following the 3rd dose at 6 h, but there was appreciable overlap of the trough concentrations for 75 mg IV q6h and 50 mg IV q4h between 24 and 42 h. The pre-dose concentrations as well as the concentrations after the last dose at 42 h were higher for 100 mg PO q6h compared to both IV arms, presumably due to first pass metabolism which results in a higher fraction of the active metabolite in systemic circulation after oral administration.

Select pharmacokinetic parameters (overall Cmax, Cmax at steady-state, trough at steady-state, AUC over the last dosing interval for each regimen, ie, $AUC_{tau\ n}$) for tramadol are summarized in Table 1 below.

TABLE 1

Additional Plasma Pharmacokinetic Parameters of Tramadol

| | 75 mg IV | | | | 50 mg IV | | | | 100 mg Oral | | | |
|---|---|---|---|---|---|---|---|---|---|---|---|---|
| Parameter | n | Mean | SD | CV % | n | Mean | SD | CV % | n | Mean | SD | CV % |
| $C_{max}$ (ng/mL) | 14 | 932 | 199 | 21.30 | 14 | 736 | 152 | 20.60 | 17 | 701 | 178 | 25.44 |
| $C_{max(42-48)}$ (ng/mL) | 14 | 827 | 234 | 28.24 | — | — | — | — | 17 | 701 | 178 | 25.44 |
| $C_{max(44-48)}$ (ng/mL) | — | — | — | — | 14 | 711 | 152 | 21.40 | — | — | — | — |
| $T_{48}$ (ng/mL) | 14 | 354 | 85.9 | 24.31 | 14 | 448 | 131 | 29.36 | 17 | 497 | 144 | 29.09 |
| Css (ng/mL) | 14 | 506 | 101 | 20.03 | 14 | 557 | 131 | 23.60 | 17 | 579 | 150 | 25.96 |

Exposure to O-desmethyltramadol was higher after 100 mg PO q6h compared to either IV treatment, 50 mg IV q4h or 75 mg IV q6h. This was expected, considering the first pass metabolism after oral administration. Although exposure parameters were slightly higher for 75 mg IV q6h compared to 50 mg IV q4h through early time points, exposure to 0-desmethyltramadol was comparable for the two IV regimens when the entire pharmacokinetic sampling period was considered. For example, the mean Css for O-desmethyltramadol was 86.6 ng/mL for 75 mg IV q6h and 88.9 ng/mL for 50 mg IV q4h; the mean Css for 100 mg PO q6h was higher, at 128 ng/mL. This is understandable taking into account the similarity in the total IV doses administered in the study (650 mg for the 50 mg IV q4h arm, 675 mg for the 75 mg IV q6h arm) and the slightly higher oral dose (800 mg for the 100 mg PO q6h arm).

The observed mean (STD) tramadol plasma concentration versus time curve for IV 50 mg and oral 100 mg as well as the fitted curve for the oral 100 mg for the initial 12 hours after administration was obtained because the second oral peak was not measured in the study. The model fit was very good, with the curve demonstrating the concentrations of the IV 50 mg regimen are generally higher after the Hour 2 dose. The 50 mg IV regimen was very close to steady-state after the 3rd dose, due to the loading dose strategy (comparable Cmax after the hour 4 dose to Cmax after the Hour 44 dose), and the oral Cmax was achieved later but reaches a similar level to the 50 mg IV regimen.

Plasma pharmacokinetic parameters for tramadol in Example 5 are set forth in Table 2 below:

TABLE 2

| | 75 mg IV | | | | 50 mg IV | | | | 100 mg Oral | | | |
|---|---|---|---|---|---|---|---|---|---|---|---|---|
| Parameter | n | Mean | SD | CV % | n | Mean | SD | CV % | n | Mean | SD | CV % |
| $T_{max}$ (h) | 14 | 15.93 | 17.36 | 108.96 | 14 | 30.02 | 19.89 | 66.27 | 17 | 44.03 | 1.01 | 2.29 |
| $C_{max}$ (ng/mL) | 14 | 932 | 199 | 21.30 | 14 | 736 | 152 | 20.60 | 17 | 701 | 178 | 25.44 |
| $C_{1h}$ (ng/mL) | 14 | 361 | 63.8 | 17.65 | 14 | 243 | 45.2 | 18.56 | 17 | 278 | 77.0 | 27.72 |
| $C_2$ (ng/mL) | — | — | — | — | 14 | 203 | 31.6 | 15.59 | — | — | — | — |
| $C_3$ (ng/mL) | 14 | 237 | 41.6 | 17.53 | — | — | — | — | — | — | — | — |
| $C_6$ (ng/mL) | — | — | — | — | — | — | — | — | 17 | 197 | 55.0 | 27.93 |
| $T_{max(0-2)}$ (h) | — | — | — | — | 14 | 0.54 | 0.22 | 40.34 | — | — | — | — |
| $C_{max(0-2)}$ (ng/mL) | — | — | — | — | 14 | 294 | 68.5 | 23.27 | — | — | — | — |
| $T_{max(0-3)}$ (h) | 14 | 0.50 | 0.28 | 55.47 | — | — | — | — | — | — | — | — |
| $C_{max(0-3)}$ (ng/mL) | 14 | 484 | 155 | 31.93 | — | — | — | — | — | — | — | — |
| $T_{max(0-6)}$ (h) | — | — | — | — | — | — | — | — | 17 | 1.54 | 0.33 | 21.60 |
| $C_{max(0-6)}$ (ng/mL) | — | — | — | — | — | — | — | — | 17 | 377 | 68.9 | 18.31 |
| $T_{max(2-4)}$ (h) | — | — | — | — | 14 | 2.36 | 0.13 | 5.40 | — | — | — | — |
| $C_{max(2-4)}$ (ng/mL) | — | — | — | — | 14 | 479 | 77.7 | 16.23 | — | — | — | — |
| $T_{max(3-6)}$ (h) | 14 | 3.31 | 0.11 | 3.19 | — | — | — | — | — | — | — | — |
| $C_{max(3-6)}$ (ng/mL) | 14 | 756 | 141 | 18.65 | — | — | — | — | — | — | — | — |
| $T_{max(42-48)}$ (h) | 14 | 42.38 | 0.19 | 0.45 | — | — | — | — | 17 | 44.03 | 1.01 | 2.29 |
| $C_{max(42-48)}$ (ng/mL) | 14 | 827 | 234 | 28.24 | — | — | — | — | 17 | 701 | 178 | 25.44 |
| $T_{max(44-48)}$ (h) | — | — | — | — | 14 | 44.30 | 0.11 | 0.24 | — | — | — | — |
| $C_{max(44-48)}$ (ng/mL) | — | — | — | — | 14 | 711 | 152 | 21.40 | — | — | — | — |
| $C_{48}$ (ng/mL) | 14 | 354 | 85.9 | 24.31 | 14 | 448 | 131 | 29.36 | 17 | 497 | 144 | 29.09 |
| $AUC_{tau\ 1}$ (h*ng/mL) | 14 | 1251 | 165.4 | 13.22 | 15 | 624.2 | 85.06 | 13.64 | 17 | 1494 | 282.3 | 18.90 |
| $AUC_{0-24}$ (h*ng/mL) | 14 | 9932 | 1958 | 19.72 | 14 | 9520 | 2106 | 22.12 | 17 | 7491 | 1936 | 25.85 |
| $AUC_{24-48}$ (h*ng/mL) | 14 | 9402 | 2511 | 26.71 | 14 | 11020 | 2852 | 25.88 | 17 | 11650 | 3387 | 29.07 |
| $AUC_{0-48}$ (h*ng/mL) | 14 | 19330 | 4427 | 22.90 | 14 | 20540 | 4906 | 23.89 | 17 | 19140 | 5172 | 27.02 |
| $AUC_{tau\ n}$ (h*ng/mL) | 14 | 3036 | 608.3 | 20.04 | 14 | 2228 | 525.6 | 23.60 | 17 | 3475 | 902.2 | 25.97 |
| $RAC(C_{max})$ | 14 | 1.7828 | 0.4975 | 27.91 | 14 | 2.4663 | 0.4953 | 20.08 | 17 | 1.8588 | 0.2858 | 15.37 |
| $RAC_{(rough)}$ | 14 | 1.5026 | 0.3613 | 24.05 | 14 | 2.1937 | 0.4768 | 21.74 | 17 | 2.5580 | 0.4577 | 17.89 |
| $RAC(AUC_{tau})$ | 14 | 2.4314 | 0.4060 | 16.70 | 14 | 3.5359 | 0.4662 | 13.18 | 17 | 2.3211 | 0.3437 | 14.81 |
| Css (ng/mL) | 14 | 506 | 101 | 20.03 | 14 | 557 | 131 | 23.60 | 17 | 579 | 150 | 25.96 |
| P/T Ratio First | 14 | 2.0658 | 0.6131 | 29.68 | 14 | 1.4566 | 0.2812 | 19.31 | 17 | 1.9824 | 0.3664 | 18.48 |
| P/T Ratio Last | 14 | 2.3692 | 0.5090 | 21.48 | 14 | 1.6370 | 0.2655 | 16.22 | 17 | 1.4400 | 0.2286 | 15.87 |

Plasma pharmacokinetic parameters of the O-desmethyltramadol metabolite in the study of Example 1 are set forth in Table 3:

TABLE 3

| | 75 mg IV | | | | 50 mg IV | | | | 100 mg Oral | | | |
|---|---|---|---|---|---|---|---|---|---|---|---|---|
| Parameter | n | Mean | SD | CV % | n | Mean | SD | CV % | n | Mean | SD | CV % |
| $T_{max}$ (h) | 14 | 32.99 | 16.50 | 50.01 | 14 | 44.95 | 1.59 | 3.53 | 17 | 43.97 | 1.12 | 2.54 |
| $C_{max}$ (ng/mL) | 14 | 99.2 | 25.6 | 25.85 | 14 | 96.6 | 24.5 | 25.35 | 17 | 146 | 37.4 | 25.62 |
| $C_{1\ h}$ (ng/mL) | 14 | 19.9 | 6.65 | 33.32 | 14 | 11.8 | 4.57 | 38.82 | 17 | 41.4 | 19.7 | 47.47 |
| $C_2$ (ng/mL) | — | — | — | — | 14 | 16.9 | 6.47 | 38.32 | — | — | — | — |
| $C_3$ (ng/mL) | 14 | 29.5 | 10.0 | 33.87 | — | — | — | — | — | — | — | — |
| $C_6$ (ng/mL) | — | — | — | — | — | — | — | — | 17 | 42.3 | 13.6 | 32.19 |
| $T_{max(0-2)}$ (h) | — | — | — | — | 14 | 1.85 | 0.19 | 10.34 | — | — | — | — |
| $C_{max(0-2)}$ (ng/mL) | — | — | — | — | 14 | 17.1 | 6.46 | 37.91 | — | — | — | — |
| $T_{max(0-3)}$ (h) | 14 | 2.71 | 0.49 | 18.03 | — | — | — | — | — | — | — | — |
| $C_{max(0-3)}$ (ng/mL) | 14 | 29.7 | 10.2 | 34.28 | — | — | — | — | — | — | — | — |
| $T_{max(0-6)}$ (h) | — | — | — | — | — | — | — | — | 17 | 2.04 | 0.87 | 42.42 |
| $C_{max(0-6)}$ (ng/mL) | — | — | — | — | — | — | — | — | 17 | 60.3 | 22.7 | 37.60 |
| $T_{max(2-4)}$ (h) | — | — | — | — | 14 | 3.95 | 0.00 | 0.00 | — | — | — | — |
| $C_{max(2-4)}$ (ng/mL) | — | — | — | — | 14 | 37.8 | 15.5 | 40.86 | — | — | — | — |
| $T_{max(3-6)}$ (h) | 14 | 5.81 | 0.52 | 8.98 | — | — | — | — | — | — | — | — |
| $C_{max(3-6)}$ (ng/mL) | 14 | 59.4 | 18.6 | 31.34 | — | — | — | — | — | — | — | — |
| $T_{max(42-48)}$ (h) | 14 | 43.10 | 0.36 | 0.84 | — | — | — | — | 17 | 43.97 | 1.12 | 2.54 |
| $C_{max(42-48)}$ (ng/mL) | 14 | 96.7 | 25.1 | 25.99 | — | — | — | — | 17 | 146 | 37.4 | 25.62 |
| $T_{max(44-48)}$ (h) | — | — | — | — | 14 | 45.31 | 0.68 | 1.50 | — | — | — | — |
| $C_{max(44-48)}$ (ng/mL) | — | — | — | — | 14 | 96.2 | 24.5 | 25.46 | — | — | — | — |
| $C_{48}$ (ng/mL) | 14 | 75.9 | 22.4 | 29.48 | 14 | 81.7 | 20.2 | 24.68 | 17 | 111 | 31.5 | 28.33 |
| $AUC_{tau\ 1}$ (h*ng/mL) | 14 | 108.3 | 35.79 | 33.06 | 15 | 39.93 | 15.89 | 39.77 | 17 | 272.1 | 97.32 | 35.77 |
| $AUC_{0-24}$ (h*ng/mL) | 14 | 1608 | 428.2 | 26.63 | 14 | 1425 | 405.4 | 28.44 | 17 | 1655 | 476.6 | 28.79 |
| $AUC_{24-48}$ (h*ng/mL) | 14 | 1896 | 524.5 | 27.66 | 14 | 2002 | 514.9 | 25.72 | 17 | 2693 | 750.0 | 27.85 |
| $AUC_{0-48}$ (h*ng/mL) | 14 | 3504 | 931.2 | 26.58 | 14 | 3427 | 889.9 | 25.97 | 17 | 4349 | 1139 | 26.20 |
| $AUC_{tau\ n}$ (h*ng/mL) | 15 | 519.8 | 142.7 | 27.45 | 14 | 355.6 | 89.39 | 25.14 | 17 | 768.4 | 209.4 | 27.26 |
| $RAC(C_{max})$ | 14 | 3.4575 | 0.8063 | 23.32 | 14 | 6.0794 | 1.4574 | 23.97 | 17 | 2.7316 | 1.2718 | 46.56 |
| $RAC_{(trough)}$ | 14 | 2.7237 | 0.7000 | 25.70 | 14 | 5.2872 | 1.4637 | 27.68 | 17 | 2.7839 | 1.0135 | 36.41 |
| $RAC(AUC_{tau})$ | 14 | 5.0884 | 1.2051 | 23.68 | 14 | 9.7100 | 2.6019 | 26.80 | 17 | 3.1287 | 1.5078 | 48.19 |
| Css (ng/mL) | 14 | 86.6 | 23.8 | 27.44 | 14 | 88.9 | 22.3 | 25.14 | 17 | 128 | 34.9 | 27.25 |
| P/T Ratio First | 14 | 1.0049 | 0.0185 | 1.84 | 14 | 1.0122 | 0.0327 | 3.23 | 17 | 1.3982 | 0.1890 | 13.52 |
| P/T Ratio Last | 14 | 1.2878 | 0.1073 | 8.33 | 14 | 1.1782 | 0.0772 | 6.55 | 17 | 1.3302 | 0.1635 | 12.29 |
| M/P Ratio $C_{1\ h}$ | 14 | 0.0571 | 0.0232 | 40.64 | 14 | 0.0503 | 0.0224 | 44.54 | 17 | 0.1579 | 0.0798 | 50.54 |
| M/P Ratio $T_{48}$ | 14 | 0.2266 | 0.0796 | 35.14 | 14 | 0.2002 | 0.0794 | 39.67 | 17 | 0.2423 | 0.0929 | 38.33 |

The term "STD" as used herein means standard deviation. The term "C2" means plasma concentration of tramadol at time 2 or hour 2 (in other words, the tramadol plasma concentration at 2 hours after the first administered tramadol dose). The term "C3" means plasma concentration of tramadol at time 3 or hour 3 (in other words, the tramadol plasma concentration at 3 hours after the first administered tramadol dose). The term "C6" as used herein means plasma concentration of tramadol at time 6 or hour 6 (in other words, the tramadol plasma concentration at 6 hours after the first administered tramadol dose). The term "C48" as used herein means plasma concentration of tramadol at time 48 or hour 48 (in other words, the tramadol plasma concentration at 48 hours after the first administered tramadol dose). The term "$C_{ss}$" means steady-state concentration. The term "$C_{max}$" means maximum concentration. The term "AUC" means area under the curve. The term "$AUC_{tau}$" means area under the plasma concentration-time curve over the dosing interval. As opposed to $AUC_{(0-inf)}$ which is extrapolated out to infinity, $AUC_{tau\ n}$ is the AUC in the last dosing interval (for example, with respect to the 50 mg dosing regimen, that would be at 44-48 hours from first dose). The term "RAC" means ratio of accumulation from first dose to steady-state. (Thus, if a patient had a $C_{max}$ of 500 ng/ml in the first interval, and 1000 ng/mL at steady-state, the RAC is 1000/500=2.0). The term "P/T" means peak to trough. The term "M/P" means metabolite to parent (tramadol) ratio.

The mean tramadol $C_{max}$ for the first dose ranged from 294 ng/mL after 50 mg IV ($C_{max(0-2)}$) to 484 ng/mL after 75 mg IV ($C_{max(0-3)}$); the $C_{max}$ after the first 100 mg PO ($C_{max(0-6)}$) was 377 ng/mL. Over the entire pharmacokinetic sampling period, the $C_{max}$ for 75 mg IV q6h was somewhat higher, 932 ng/mL, compared to the other treatments. The $C_{max}$ after 50 mg IV q4h and 100 mg PO q6h were similar, at 736 ng/mL and 701 ng/mL, respectively. Of particular note, the $C_{max}$ at steady-state for 50 mg IV was 711 ng/ml, while for the oral dose it was 701 ng/mL.

The higher peak concentrations for 75 mg IV q6h was reflected in the fluctuation between the peak and trough concentration; the P/T Ratios for the first and last doses of 75 mg IV q6h were larger (2.0658 to 2.3692) than those observed for 50 mg IV q4h (1.4566 to 1.6370) and 100 mg PO q6h (1.4400 to 1.9824). This result was expected, considering longer 6-hour dosing interval for the 75 mg IV treatment, compared to the 50 mg IV treatment, and more time for drug elimination prior to subsequent dosing.

During the last 24-hour sampling period ($AUC_{24-48}$), the exposure to tramadol after 100 mg PO q6h (11650 h*ng/mL) was comparable to that after 50 mg IV q4h (11020 h*ng/mL); the $AUC_{24-48}$ for 75 mg IV q6h was somewhat lower (9932 h*ng/mL). Two additional AUCs were calculated at the time of pharmacokinetic analysis, $AUC_{tau\ 1}$ (the AUC during the first dosing interval) and $AUC_{tau\ n}$ (the AUC during the last dosing interval). $AUC_{tau\ 1}$ and $AUC_{tau\ n}$ were used to provide another measure of the accumulation during multiple dosing. $AUC_{tau\ n}$ was used to characterize the exposure at steady-state during a consistent regimen. Although $AUC_{tau\ n}$ cannot be compared directly across all treatments, due to the different dosing intervals of 4 or 6 h, these AUCs can be used to estimate systemic exposure over a given multiple of these intervals, such as 12 h. The predicted exposure over 12 h at steady state was comparable for 50 mg IV q4h (3×2228=6684 h*ng/mL) and 100 mg PO q6h (2×3475=6950 h*ng/mL), but somewhat lower for 75 mg IV q6h (2×3036=6072 h*ng/mL). These values correlate well with the average concentration at steady-state (Css), at 557 ng/mL and 579 ng/mL for 50 mg IV q4h and 100 mg PO q6h, respectively, and 506 ng/mL for 75 mg IV q6h.

The accumulation factors for tramadol ranged from 1.5026 to 2.4314 for 75 mg IV q6h, from 2.1937 to 3.5359 for 50 mg IV q4h, and from 1.8588 to 2.5580 for 100 mg PO q6h. Overall, these values are in good agreement with the theoretical accumulation factors of 1.82 for a 6-h dosing interval and 2.42 for a 4-h dosing interval, calculated as $1/[1-\exp(-\ln 2 \cdot tau/T_{1/2})]$ and using $T_{1/2}$ of approximately 5.2 h. The shorter dosing interval results in a higher degree of accumulation at steady-state, relative to the concentrations observed after the first dose, but less fluctuation in the concentrations during the dosing interval.

The 75 mg IV/100 mg PO ratios ranged from 74.67 to 137.94%, indicating higher exposure to tramadol after 75 mg IV q6h compared to 100 mg PO q6h in general, most apparent through 24 hours. Based on the 80.00-125.00% acceptance criteria for the 90% confidence intervals, $AUC_{0-48}$ was not significantly different between these treatments. The 50 mg IV/100 mg PO ratios ranged from 89.82 to 127.81%, and only $AUC_{0-24}$ had 90% confidence intervals outside the 80.00-125.00% range; $C_{max}$, $AUC_{24-48}$, $AUC_{0-48}$, and $T_{48}$ were not significantly different between these treatments. The 75 mg IV/50 mg IV ratios ranged from 83.13 to 129.16%; although the AUCs were not significantly different across these treatments, the $C_{max}$ and $T_{48}$ concentrations were, reflecting the more pronounced fluctuation in tramadol concentrations for the 75 mg IV q6h arm.

Exposure to O-desmethyltramadol was higher after 100 mg PO q6h compared to either IV treatment, 50 mg IV q4h or 75 mg IV q6h. This was expected, considering the first pass metabolism after oral administration. Although exposure parameters were slightly higher for 75 mg IV q6h compared to 50 mg IV q4h through early time points, exposure to 0-desmethyltramadol was comparable for the two IV regimens when the entire pharmacokinetic sampling period was considered. For example, the mean Css for O-desmethyltramadol was 86.6 ng/mL for 75 mg IV q6h and 88.9 ng/mL for 50 mg IV q4h; the mean Css for 100 mg PO q6h was higher, at 128 ng/mL. This is understandable taking into account the similarity in the total IV doses administered in the study (650 mg for the 50 mg IV q4h arm, 675 mg for the 75 mg IV q6h arm) and the slightly higher oral dose (800 mg for the 100 mg PO q6h arm).

The following conclusions are drawn from Example 1: (1) the 50 mg IV regimen, as compared to the 75 mg IV regimen, resulted in less peak to trough fluctuation with lower Cmax. This regimen also provided a pharmacokinetic profile very similar to the 100 mg oral dose regimen; and (2) exposure to O-desmethyltramadol was higher after 100 mg PO q6h compared to either IV treatment, 50 mg IV or 75 mg IV regimens, based on AUC and Cmax values; (3) overall Cmax was comparable between the 50 mg IV and 100 mg PO regimens; exposure at steady-state to tramadol, based on Cmax and AUC, was also comparable between 50 mg IV q4h and 100 mg PO q6h; (4) administration of a lower IV dose more frequently, as in the 50 mg IV q4h regimen compared to the 75 mg IV q6 regimen, resulted in less fluctuation during the dosing interval and a pharmacokinetic profile very similar to the 100 mg oral dose; (5) compared to the 50 mg IV q4h and 100 mg PO q6h regimens, greater peak to trough variance in tramadol concentrations was observed for the 75 mg IV q6h regimen. The data from Example 1 demonstrate that the 50 mg IV dosing regimen (with tramadol 50 mg at Hour 0, followed by 50 mg at Hour 2, 50 mg at hour 4, and 50 mg every 4 hours thereafter through Hour 44) provides a Cmax and AUC that is similar to the steady-state Cmax and AUC of an oral dose of 100 mg tramadol HCl administered every six hours.

Example 2

This invention is further described below with respect to data prospectively generated as set forth below. Example 2 depicts a 25 mg intravenous dose of tramadol 25 mg at Hour 0, followed by 25 mg tramadol at Hour 2, 25 mg tramadol at hour 4, and 25 mg tramadol every 4 hours thereafter through Hour 44. The 25 mg IV dose plasma concentrations and pharmacokinetic parameters were based on data generated in Example 1, assuming dose proportionality from the 50 mg IV dose and a % CV which independent of magnitude. The software used are plots of plasma-concentration vs. time for both tramadol and o-desmethyltramadol created in Phoenix WinNonlin 6.4. Tables were generated using both Microsoft Word and Excel.

Table 4 provides plasma pharmacokinetic parameters of intravenous tramadol 25 mg dosing regimen.

TABLE 4

| | | 25 mg IV | | |
|---|---|---|---|---|
| Parameter | n | Mean | SD | CV % |
| $T_{max}$ (h) | 14 | 30.02 | 19.89 | 66.27 |
| $C_{max}$ (ng/mL) | 14 | 368 | 76 | 20.60 |
| $C_{1\,h}$ (ng/mL) | 14 | 122 | 23 | 18.56 |
| $T_2$ (ng/mL) | 14 | 102 | 16 | 15.59 |
| $T_3$ (ng/mL) | — | — | — | — |
| $T_6$ (ng/mL) | — | — | — | — |
| $T_{max(0-2)}$ (h) | 14 | 0.54 | 0.22 | 40.34 |
| $C_{max(0-2)}$ (ng/mL) | 14 | 147 | 34 | 23.27 |
| $T_{max(0-3)}$ (h) | — | — | — | — |
| $C_{max(0-3)}$ (ng/mL) | — | — | — | — |
| $T_{max(0-6)}$ (h) | — | — | — | — |
| $C_{max(0-6)}$ (ng/mL) | — | — | — | — |
| $T_{max(2-4)}$ (h) | 14 | 2.36 | 0.13 | 5.40 |
| $C_{max(2-4)}$ (ng/mL) | 14 | 240 | 39 | 16.23 |
| $T_{max(3-6)}$ (h) | — | — | — | — |
| $C_{max(3-6)}$ (ng/mL) | — | — | — | — |
| $T_{max(42-48)}$ (h) | — | — | — | — |
| $C_{max(42-48)}$ (ng/mL) | — | — | — | — |
| $T_{max(44-48)}$ (h) | 14 | 44.3 | 0.11 | 0.24 |
| $C_{max(44-48)}$ (ng/mL) | 14 | 356 | 76 | 21.40 |
| $T_{48}$ (ng/mL) | 14 | 224 | 66 | 29.36 |
| $AUC_{tau\,1}$ (h * ng/mL) | 15 | 312 | 43 | 13.64 |
| $AUC_{0-24}$ (h * ng/mL) | 14 | 4760 | 1053 | 22.12 |
| $AUC_{24-48}$ (h * ng/mL) | 14 | 5510 | 1426 | 25.88 |
| $AUC_{0-48}$ (h * ng/mL) | 14 | 10270 | 2453 | 23.89 |
| $AUC_{tau\,n}$ (h * ng/mL) | 14 | 1114 | 263 | 23.6 |
| RAC ($C_{max}$) | 14 | 2.4663 | 0.4953 | 20.08 |
| RAC$_{(trough)}$ | 14 | 2.1937 | 0.4768 | 21.74 |
| RAC ($AUC_{tau}$) | 14 | 3.5359 | 0.4662 | 13.18 |
| Css (ng/mL) | 14 | 279 | 66 | 23.60 |
| P/T Ratio First | 14 | 1.4566 | 0.2812 | 19.31 |
| P/T Ratio Last | 14 | 1.637 | 0.2655 | 16.22 |

Table 5 provides plasma pharmacokinetic parameters of O-desmethyltramadol for the dosing regimen of Example 2.

TABLE 5

| | | 25 mg IV | | |
|---|---|---|---|---|
| Parameter | n | Mean | SD | CV % |
| $T_{max}$ (h) | 14 | 44.95 | 1.59 | 3.53 |
| $C_{max}$ (ng/mL) | 14 | 48.3 | 12.3 | 25.35 |

TABLE 5-continued

| | 25 mg IV | | | |
|---|---|---|---|---|
| Parameter | n | Mean | SD | CV % |
| $C_{1\,h}$ (ng/mL) | 14 | 5.9 | 2.3 | 38.82 |
| $T_2$ (ng/mL) | 14 | 8.5 | 3.2 | 38.32 |
| $T_3$ (ng/mL) | — | — | — | — |
| $T_6$ (ng/mL) | — | — | — | — |
| $T_{max(0-2)}$ (h) | 14 | 1.85 | 0.19 | 10.34 |
| $C_{max(0-2)}$ (ng/mL) | 14 | 8.6 | 3.2 | 37.91 |
| $T_{max(0-3)}$ (h) | — | — | — | — |
| $C_{max(0-3)}$ (ng/mL) | — | — | — | — |
| $T_{max(0-6)}$ (h) | — | — | — | — |
| $C_{max(0-6)}$ (ng/mL) | — | — | — | — |
| $T_{max(2-4)}$ (h) | 14 | 3.95 | 0 | 0 |
| $C_{max(2-4)}$ (ng/mL) | 14 | 18.9 | 7.8 | 40.86 |
| $T_{max(3-6)}$ (h) | — | — | — | — |
| $C_{max(3-6)}$ (ng/mL) | — | — | — | — |
| $T_{max(42-48)}$ (h) | — | — | — | — |
| $C_{max(42-48)}$ (ng/mL) | — | — | — | — |
| $T_{max(44-48)}$ (h) | 14 | 45.31 | 0.68 | 1.50 |
| $C_{max(44-48)}$ (ng/mL) | 14 | 48.1 | 12.3 | 25.46 |
| $T_{48}$ (ng/mL) | 14 | 40.9 | 10.1 | 24.68 |
| $AUC_{tau\,1}$ (h * ng/mL) | 15 | 20.0 | 7.9 | 39.77 |
| $AUC_{0-24}$ (h * ng/mL) | 14 | 712.5 | 202.7 | 28.44 |
| $AUC_{24-48}$ (h * ng/mL) | 14 | 1001.0 | 257.5 | 25.72 |
| $AUC_{0-48}$ (h * ng/mL) | 14 | 1713.5 | 445.0 | 25.97 |
| $AUC_{tau\,n}$ (h * ng/mL) | 14 | 177.8 | 44.7 | 25.14 |
| RAC ($C_{max}$) | 14 | 6.0794 | 1.4574 | 23.97 |
| RAC$_{(trough)}$ | 14 | 5.2872 | 1.4637 | 27.68 |
| RAC ($AUC_{tau}$) | 14 | 9.71 | 2.6019 | 26.80 |
| Css (ng/mL) | 14 | 44.5 | 11.2 | 25.14 |
| P/T Ratio First | 14 | 1.0122 | 0.0327 | 3.23 |
| P/T Ratio Last | 14 | 1.1782 | 0.0772 | 6.55 |
| M/P Ratio $C_{1\,h}$ | 14 | 0.0503 | 0.0224 | 44.54 |
| M/P Ratio $T_{48}$ | 14 | 0.2002 | 0.0794 | 39.67 |

Example 3

This invention is further described below in an alternate embodiment with respect to data prospectively generated as set forth below. Example 3 depicts a 25 mg intravenous dose of tramadol 25 mg at Hour 0, followed by 50 mg tramadol at Hour 2, 25 mg tramadol at hour 4, and 25 mg tramadol every 4 hours thereafter through Hour 44.

Figure 2:
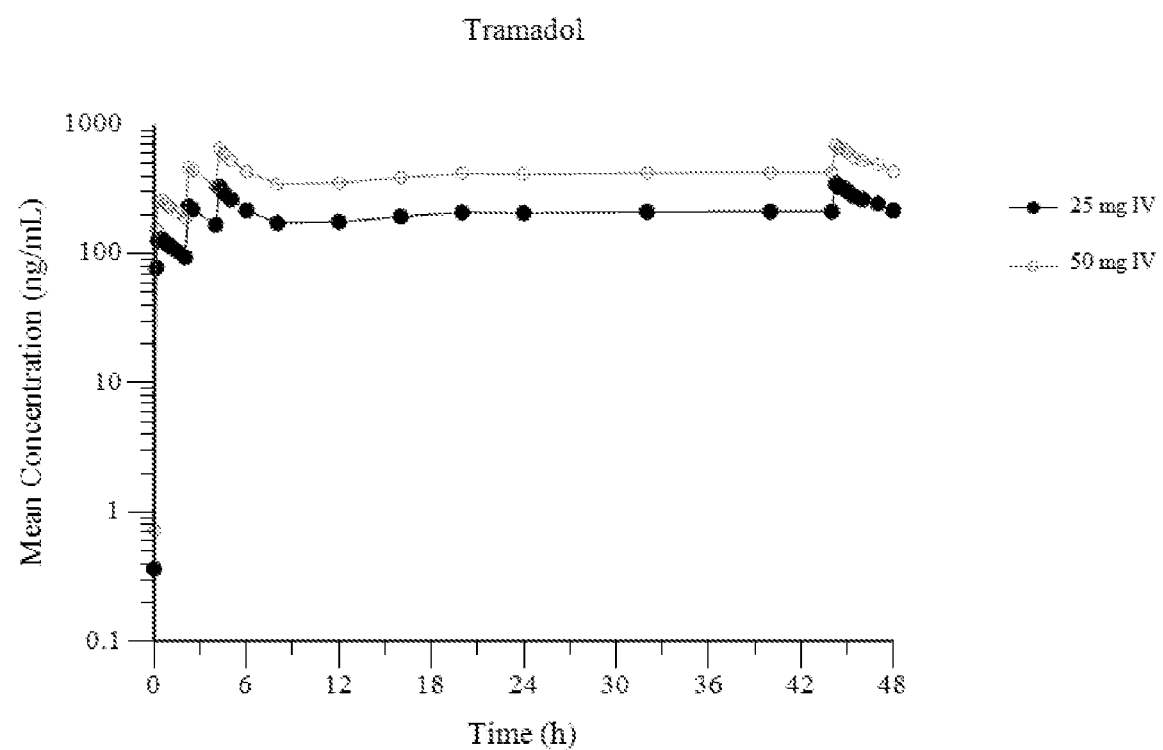
FIG. 2 provides a mean plasma concentration-time profile (log scale) for intravenous tramadol administered at a dose of 25 mg as per Example 2.
Figure 3:
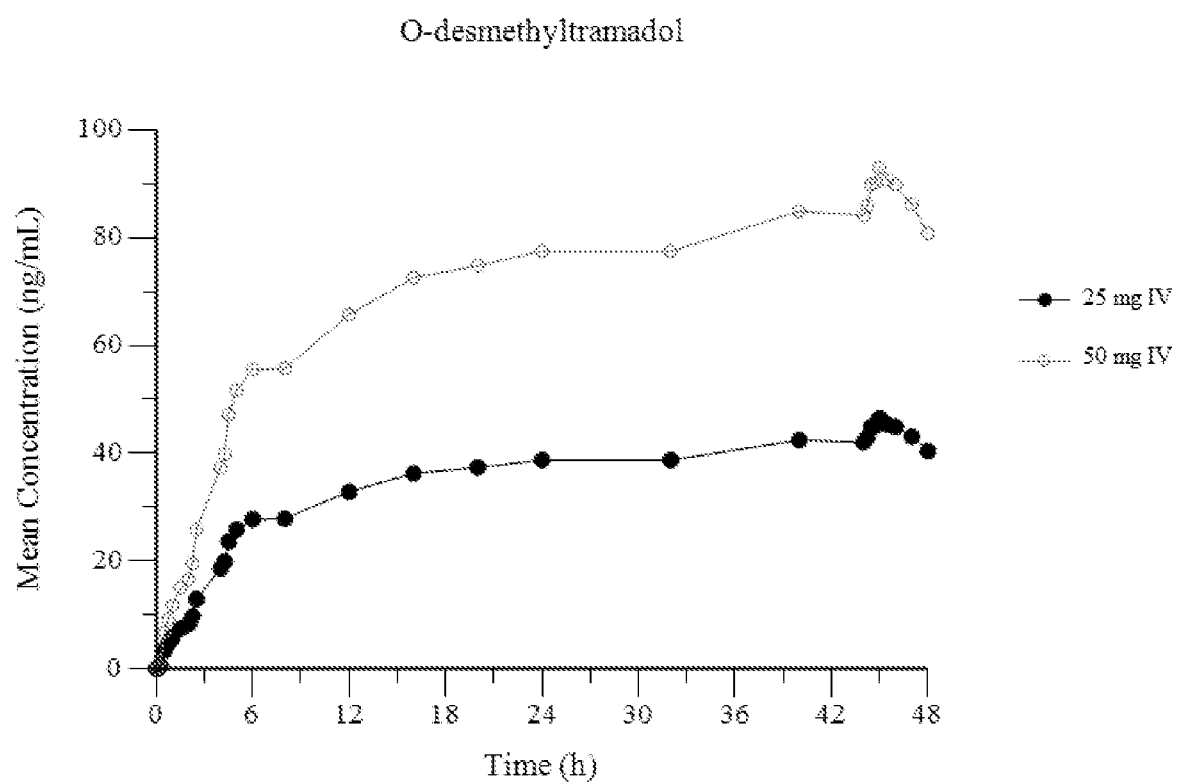
FIG. 3 provides a mean plasma concentration-time profile (linear scale) for 0-Desmethyltramadol when intravenous tramadol is administered at a dose of 25 mg as per Example 2.
Figure 4:
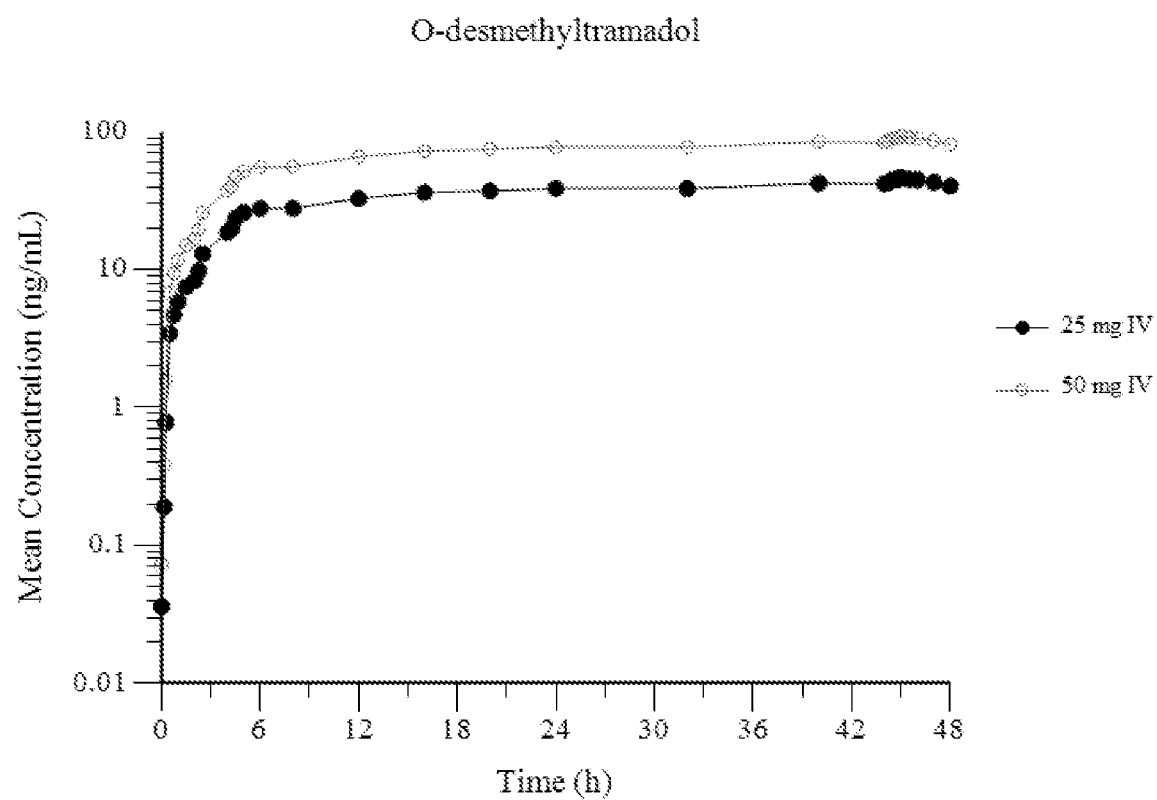
FIG. 4 provides a mean plasma concentration-time profile (log scale) for 0-Desmethyltramadol when intravenous tramadol is administered at a dose of 25 mg as per Example 2.

FIG. 1 provides a mean plasma concentration-time profile (linear scale) for intravenous tramadol administered at a dose of 25 mg at Hour 0, followed by 50 mg at Hour 2, 25 mg at hour 4, and 25 mg every 4 hours thereafter through Hour 44; and comparatively provides a mean plasma concentration-time profile (linear scale) for intravenous tramadol administered at a dose of 50 mg at Hour 0, followed by 50 mg at Hour 2, 50 mg at hour 4, and 50 mg every 4 hours thereafter through Hour 44. FIG. 2 provides a mean plasma concentration-time profile (log scale) for intravenous tramadol administered at a dose of 25 mg at Hour 0, followed by 50 mg at Hour 2, 25 mg at hour 4, and 25 mg every 4 hours thereafter through Hour 44; and comparatively provides a mean plasma concentration-time profile (log scale) for intravenous tramadol administered at a dose of 50 mg at Hour 0, followed by 50 mg at Hour 2, 50 mg at hour 4, and 50 mg every 4 hours thereafter through Hour 44. FIG. 3 provides a mean plasma concentration-time profile (linear scale) for O-Desmethyltramadol when intravenous tramadol is administered at a dose of 25 mg at Hour 0, followed by 50 mg at Hour 2, 25 mg at hour 4, and 25 mg every 4 hours thereafter through Hour 44; and comparatively provides a mean plasma concentration-time profile (linear scale) for intravenous tramadol administered at a dose of 50 mg at Hour 0, followed by 50 mg at Hour 2, 50 mg at hour 4, and 50 mg every 4 hours thereafter through Hour 44. FIG. 4 provides a mean plasma concentration-time profile (log scale) for O-Desmethyltramadol when intravenous tramadol is administered at a dose of 25 mg at Hour 0, followed by 50 mg at Hour 2, 25 mg at hour 4, and 25 mg every 4 hours thereafter through Hour 44; and comparatively provides a mean plasma concentration-time profile (log scale) for intravenous tramadol administered at a dose of 50 mg at Hour 0, followed by 50 mg at Hour 2, 50 mg at hour 4, and 50 mg every 4 hours thereafter through Hour 44.

Table 6 provides summary statistics concerning plasma concentrations of tramadol 25 mg IV of Example 2 (with a 50 mg loading dose at hour 2) as compared to tramadol 50 mg IV administered as set forth above. Table 7 provides summary statistics concerning plasma concentrations for O-Desmethyltramadol when tramadol 25 mg is administered intravenously as set forth in Example 2 (with a 50 mg loading dose at hour 2) as compared to plasma concentrations for O-Desmethyltramadol when tramadol 50 mg IV administered as set forth above.

TABLE 6

| | Tramadol | | | | | | |
|---|---|---|---|---|---|---|---|
| | 25 mg IV Dose Concentrations | | | | 50 mg IV Dose Concentrations | | |
| Time (hr) | N | Mean (ng/mL) | SD (ng/mL) | CV % | N | Mean (ng/mL) | SD (ng/mL) | CV % |
| 0.00 | 17 | 0.3629 | 1.084 | 299 | 17 | 0.7259 | 2.169 | 299 |
| 0.150 | 17 | 77.76 | 30.20 | 39 | 17 | 155.5 | 60.40 | 39 |
| 0.250 | 17 | 126.6 | 51.82 | 41 | 17 | 253.1 | 103.6 | 41 |
| 0.500 | 17 | 130.5 | 41.34 | 32 | 17 | 261.0 | 82.69 | 32 |
| 0.750 | 17 | 121.4 | 35.60 | 29 | 17 | 242.9 | 71.20 | 29 |
| 1.00 | 17 | 115.4 | 33.79 | 29 | 17 | 230.8 | 67.59 | 29 |
| 1.50 | 17 | 105.0 | 29.13 | 28 | 17 | 210.0 | 58.25 | 28 |
| 2.00 | 17 | 94.12 | 26.58 | 28 | 17 | 188.2 | 53.15 | 28 |
| 2.25 | 17 | 234.1 | 37.88 | 16 | 17 | 468.3 | 75.76 | 16 |
| 2.50 | 17 | 221.0 | 32.29 | 15 | 17 | 442.1 | 64.58 | 15 |
| 4.00 | 17 | 167.7 | 23.31 | 14 | 17 | 335.4 | 46.62 | 14 |
| 4.25 | 17 | 330.9 | 61.10 | 18 | 17 | 661.7 | 122.2 | 18 |
| 4.50 | 17 | 295.9 | 42.97 | 15 | 17 | 591.8 | 85.94 | 15 |
| 5.00 | 17 | 263.6 | 38.56 | 15 | 17 | 527.3 | 77.12 | 15 |
| 6.00 | 17 | 216.5 | 39.26 | 18 | 17 | 433.1 | 78.52 | 18 |
| 8.00 | 17 | 173.2 | 36.61 | 21 | 17 | 346.4 | 73.22 | 21 |
| 12.0 | 17 | 176.6 | 45.65 | 26 | 17 | 353.1 | 91.30 | 26 |

TABLE 6-continued

| | | Tramadol | | | | | | |
|---|---|---|---|---|---|---|---|---|
| | | 25 mg IV Dose Concentrations | | | | 50 mg IV Dose Concentrations | | |
| Time (hr) | N | Mean (ng/mL) | SD (ng/mL) | CV % | N | Mean (ng/mL) | SD (ng/mL) | CV % |
| 16.0 | 17 | 194.1 | 53.08 | 27 | 17 | 388.2 | 106.2 | 27 |
| 20.0 | 17 | 209.6 | 62.28 | 30 | 17 | 419.2 | 124.6 | 30 |
| 24.0 | 17 | 206.7 | 55.99 | 27 | 17 | 413.4 | 112.0 | 27 |
| 32.0 | 17 | 211.0 | 54.86 | 26 | 17 | 422.1 | 109.7 | 26 |
| 40.0 | 17 | 211.8 | 65.69 | 31 | 17 | 423.6 | 131.4 | 31 |
| 44.0 | 17 | 211.8 | 53.61 | 25 | 17 | 423.6 | 107.2 | 25 |
| 44.3 | 17 | 348.4 | 75.04 | 22 | 17 | 696.8 | 150.1 | 22 |
| 44.5 | 17 | 327.4 | 66.46 | 20 | 17 | 654.7 | 132.9 | 20 |
| 44.8 | 17 | 322.4 | 62.83 | 19 | 17 | 644.8 | 125.7 | 19 |
| 45.0 | 17 | 305.0 | 59.86 | 20 | 17 | 610.0 | 119.7 | 20 |
| 45.5 | 17 | 276.5 | 60.75 | 22 | 17 | 553.1 | 121.5 | 22 |
| 46.0 | 17 | 264.0 | 61.61 | 23 | 17 | 527.9 | 123.2 | 23 |
| 47.0 | 17 | 244.8 | 65.76 | 27 | 17 | 489.5 | 131.5 | 27 |
| 48.0 | 17 | 216.8 | 61.35 | 28 | 17 | 433.6 | 122.7 | 28 |

TABLE 7

| | | O-Desmethyltramadol | | | | | | |
|---|---|---|---|---|---|---|---|---|
| | | 25 mg IV Dose Concentrations | | | | 50 mg IV Dose Concentrations | | |
| Time (hr) | N | Mean (ng/mL) | SD (ng/mL) | CV % | N | Mean (ng/mL) | SD (ng/mL) | CV % |
| 0.00 | 17 | 0.03618 | 0.1492 | 412 | 17 | 0.07235 | 0.2983 | 412 |
| 0.150 | 17 | 0.1898 | 0.2705 | 143 | 17 | 0.3796 | 0.5410 | 143 |
| 0.250 | 17 | 0.7798 | 0.5416 | 69 | 17 | 1.560 | 1.083 | 69 |
| 0.500 | 17 | 3.429 | 1.704 | 50 | 17 | 6.858 | 3.408 | 50 |
| 0.750 | 17 | 4.702 | 2.089 | 44 | 17 | 9.405 | 4.179 | 44 |
| 1.00 | 17 | 5.855 | 2.729 | 47 | 17 | 11.71 | 5.458 | 47 |
| 1.50 | 17 | 7.504 | 3.288 | 44 | 17 | 15.01 | 6.576 | 44 |
| 2.00 | 17 | 8.304 | 3.763 | 45 | 17 | 16.61 | 7.527 | 45 |
| 2.25 | 17 | 9.787 | 4.493 | 46 | 17 | 19.57 | 8.986 | 46 |
| 2.50 | 17 | 12.99 | 6.090 | 47 | 17 | 25.98 | 12.18 | 47 |
| 4.00 | 17 | 18.67 | 8.020 | 43 | 17 | 37.35 | 16.04 | 43 |
| 4.25 | 17 | 19.92 | 7.970 | 40 | 17 | 39.84 | 15.94 | 40 |
| 4.50 | 17 | 23.63 | 9.819 | 42 | 17 | 47.26 | 19.64 | 42 |
| 5.00 | 17 | 25.89 | 9.825 | 38 | 17 | 51.78 | 19.65 | 38 |
| 6.00 | 17 | 27.77 | 10.15 | 37 | 17 | 55.54 | 20.29 | 37 |
| 8.00 | 17 | 27.90 | 9.712 | 35 | 17 | 55.79 | 19.42 | 35 |
| 12.0 | 17 | 32.89 | 9.979 | 30 | 17 | 65.77 | 19.96 | 30 |
| 16.0 | 17 | 36.29 | 10.37 | 29 | 17 | 72.58 | 20.74 | 29 |
| 20.0 | 17 | 37.39 | 10.81 | 29 | 17 | 74.78 | 21.62 | 29 |
| 24.0 | 17 | 38.76 | 11.13 | 29 | 17 | 77.52 | 22.26 | 29 |
| 32.0 | 17 | 38.76 | 11.52 | 30 | 17 | 77.51 | 23.04 | 30 |
| 40.0 | 17 | 42.45 | 11.66 | 27 | 17 | 84.91 | 23.31 | 27 |
| 44.0 | 17 | 42.08 | 11.40 | 27 | 17 | 84.15 | 22.80 | 27 |
| 44.3 | 17 | 42.97 | 11.57 | 27 | 17 | 85.95 | 23.13 | 27 |
| 44.5 | 17 | 44.93 | 12.23 | 27 | 17 | 89.86 | 24.46 | 27 |
| 44.8 | 17 | 45.11 | 12.43 | 28 | 17 | 90.22 | 24.87 | 28 |
| 45.0 | 17 | 46.51 | 12.06 | 26 | 17 | 93.02 | 24.11 | 26 |
| 45.5 | 17 | 45.36 | 11.65 | 26 | 17 | 90.73 | 23.31 | 26 |
| 46.0 | 17 | 44.93 | 11.60 | 26 | 17 | 89.86 | 23.20 | 26 |
| 47.0 | 17 | 43.12 | 11.29 | 26 | 17 | 86.24 | 22.57 | 26 |
| 48.0 | 17 | 40.41 | 10.28 | 25 | 17 | 80.81 | 20.55 | 25 |

Example 4

Example 4 is a multiple dose, steady-state dose proportionality study of tramadol injection 50 mg and 100 mg administered intravenously and tramadol 50 mg and 100 mg (Ultram® tablet) administered orally in 32 healthy volunteers. The primary objective of the study was to establish the comparative bioavailability of tramadol 50 mg and 100 mg (Ultram® tablet) administered orally at steady-state relative to tramadol injection 50 mg and 100 mg administered intravenously and to establish the doses proportionality of tramadol injection at steady-state. The purpose of including this study in the present application is to provide data for the 50 mg tramadol oral dose as compared to the simulated tramadol intravenous data provided in Examples 2 and 3. The study was an open-label, single-period, randomized, parallel treatment design. Subjects received study drug every 6 hours beginning on the morning of Day 1 and ending on the morning of Day 3. The first dose on Day 1 and the last dose on Day 3 were administered after a minimum 10 hour fast. Tramadol injection was administered intravenously over 15 minutes. Tramadol injection was diluted in 50 mL of normal saline and a pump was used to standardize the administration of the injection. Tramadol tablets were administered with 240 mL of water. Blood samples for analysis of tramadol and O-desmethyltramadol (M1) plasma concentrations were obtained pre-dose (within 5 minutes prior to study drug administration) for each of the 9 doses. On day 3, blood samples were also obtained at o.083 (5 min), 0.17 (10 min) 0.25, 0.5, 0.75, 1, 1.25, 1.5, 2, 2.5, 3, 3.5, 4, 6, 8, 10, 12 18, 24 36 and 48 hours after the last dose of study drug. The primary variables were the $C_{max}$ and $AUC_6$ of tramadol (oral and IV) and M1 following the last dose.

The results for tramadol are provided in Table 8 below:

TABLE 8

| Parameter | Units | Tramadol Dosed as 50 mg IV Mean ± SD (CV %) | Tramadol Dosed as 50 mg Oral Mean ± SD (CV %) | Tramadol Dosed as 100 mg IV Mean ± SD (CV %) | Tramadol Dosed as 100 gm Oral Mean ± SD (CV %) |
|---|---|---|---|---|---|
| $C_{max}$ | ng/mL | 541 ± 126 (23.4%) | 355 ± 121 (34.1%) | 1250 ± 236 (18.6%) | 703 ± 210 (29.9%) |
| $C_{min}$ | ng/mL | 203 ± 50 (24.6%) | 213 ± 93 (43.7%) | 539 ± 172 (32.0%) | 405 ± 151 (37.4%) |
| $T_{max}$ | h | 0.375 ± 0.189 (50.4%) | 1.88 ± 0.78 (41.6%) | 0.406 ± 0.442 (108.8%) | 2.32 ± 1.35 (58.2%) |
| $AUC_6$ | ng · h/mL | 1968 ± 453 (23.0%) | 1731 ± 625 (36.1%) | 4732 ± 1239 (26.2%) | 3365 ± 1009 (30.0%) |
| $AUC_t$ | ng · h/mL | 4011 ± 1047 (26.1%) | 4363 ± 2027 (46.5%) | 11184 ± 4271 (38.2%) | 8662 ± 4258 (49.2%) |
| $AUC_\infty$ | ng · h/mL | 4038 ± 1060 (26.3%) | 4453 ± 2111 (47.4%) | 11432 ± 4542 (39.7%) | 8851 ± 4572 (51.6%) |
| Trough/Peak | Ratio | 0.387 ± 0.088 (22.8%) | 0.585 ± 0.091 (15.5%) | 0.430 ± 0.106 (24.5%) | 0.578 ± 0.154 (26.6%) |

The results for the tramadol M1 metabolite are provided in Table 9 below:

TABLE 9

| Parameter | Units | Tramadol Dosed as 50 mg IV Mean ± SD (CV %) | Tramadol Dosed as 50 mg Oral Mean ± SD (CV %) | Tramadol Dosed as 100 mg IV Mean ± SD (CV %) | Tramadol Dosed as 100 gm Oral Mean ± SD (CV %) |
|---|---|---|---|---|---|
| $C_{max}$ | ng/mL | 78.6 ± 12.4 (15.8%) | 100 ± 30 (30.0%) | 165 ± 48 (29.0%) | 130 ± 39 (29.7%) |
| $C_{min}$ | ng/mL | 55.9 ± 7.4 (13.3%) | 65.9 ± 15.8 (24.0%) | 130 ± 37 (28.7%) | 93.6 ± 34.6 (37.0%) |
| $T_{max}$ | h | 1.53 ± 0.57 (37.5%) | 2.44 ± 1.59 (65.3%) | 1.59 ± 1.04 (65.5%) | 2.25 ± 1.14 (50.7%) |
| $AUC_6$ | ng · h/mL | 398 ± 59 (14.8%) | 508 ± 139 (27.3%) | 904 ± 278 (30.7%) | 700 ± 223 (31.9%) |
| $AUC_t$ | ng · h/mL | 1086 ± 149 (13.7%) | 1454 ± 401 (27.6%) | 2733 ± 1040 (38.1%) | 2084 ± 740 (35.5%) |
| $AUC_\infty$ | ng · h/mL | 1100 ± 150 (13.6%) | 1489 ± 409 (27.5%) | 2844 ± 1187 (41.7%) | 2126 ± 739 (34.8%) |
| Trough Peak | ratio$^a$ | 0.715 ± 0.044 (6.1%) | 0.670 ± 0.061 (9.1%) | 0.795 ± 0.040 (5.0%) | 0.707 ± 0.080 (11.3%) |

Comparing the results set forth in Table 8 to the Cmax results in Table 4 and FIG. 1, it can be seen that the mean tramadol concentration for the intravenous dosing regimen provides similar steady-state peak and trough concentrations (see) as compared to a dosing regimen of 50 mg tramadol HCl administered orally every 6 hours at steady-state.

CONCLUSION

All patents and publications identified in the above paragraphs are hereby incorporated by reference in their entireties. It will be readily apparent to one of ordinary skill in the relevant arts that other suitable modifications and adaptations to the methods and applications described herein are suitable and may be made without departing from the scope of the invention or any embodiment thereof. While the invention has been described in connection with certain embodiments, it is not intended to limit the invention to the particular forms set forth, but on the contrary, it is intended to cover such alternatives, modifications and equivalents as may be included within the spirit and scope of the invention as defined by the following claims. All of the patents and publications cited herein are hereby incorporated by reference.

What is claimed is:

1. A method of administering tramadol for treating acute pain in human patients via an intravenous dosing regimen comprising intravenously administering a first dose of tramadol to human patients in an amount of about 25 mg; and thereafter intravenously administering additional doses of tramadol to the human patients in an amount of about 25 mg at dosage intervals of about 4 hours, except that a second dose is intravenously administered as a loading dose at a shortened interval as compared to the dosage interval of about 4 hours, until the patients no longer requires treatment with intravenous tramadol, wherein the tramadol is tramadol base or a pharmaceutically acceptable salt of tramadol.

2. The method of claim 1, wherein the human patients are suffering from acute post-operative pain.

3. The method of claim 1, wherein a therapeutically effective dose of an intravenous opioid analgesic is administered to the patients (i) at the end of the surgery or (ii) if the human patients request analgesia before the second dose of tramadol.

4. The method of claim 1, further comprising orally administering about 50 mg to about 100 mg tramadol to the human patients about every 6 hours after the human patients no longer require treatment with intravenous tramadol, until the human patients no longer require treatment with oral tramadol, wherein the tramadol is tramadol base or a pharmaceutically acceptable salt of tramadol.

5. The method of claim 1, wherein the dosing regimen provides a Cmax after the third intravenous dose of tramadol 25 mg, and the Cmax of the intravenous dosing regimen after the third intravenous dose of tramadol 25 mg is similar to the steady-state Cmax achieved with an oral tramadol dose of 50 mg administered every 6 hours.

6. The method of claim 1, wherein the intravenous dosing regimen provides a Cmax and AUC of tramadol which is similar to the Cmax and AUC of an oral dose of 50 mg tramadol HCl given every 6 hours at steady-state.

7. The method of claim 6, wherein such that the intravenous dosing regimen provides a Cmax of tramadol at steady-state from about 80% to about 125% of about 368 ng/mL.

8. The method of claim 7, wherein the dosing regimen provides a Cmin at steady-state, and the Cmin of tramadol at steady-state via this intravenous dosing regimen is from about 80% to about 125% of about 224 ng/ml.

9. The method of claim 2, wherein the dosing regimen provides a Cmax after the third intravenous dose of tramadol 25 mg, and the Cmax of the intravenous dosing regimen after the third intravenous dose of tramadol 25 mg is similar to the steady-state Cmax achieved with an oral tramadol dose of 50 mg administered every 6 hours.

10. The method of claim 2, wherein the intravenous dosing regimen provides a Cmax and AUC of tramadol which is similar to the Cmax and AUC of an oral dose of 50 mg tramadol HCl given every 6 hours at steady-state.

11. The method of claim 10, wherein such that the intravenous dosing regimen provides a Cmax of tramadol at steady-state from about 80% to about 125% of about 368 ng/mL.

12. The method of claim 11, wherein the dosing regimen provides a Cmin at steady-state, and the Cmin of tramadol at steady-state via this intravenous dosing regimen is from about 80% to about 125% of about 224 ng/ml.

13. The method of claim 9, wherein a therapeutically effective dose of an intravenous opioid analgesic is administered to the patients at the end of the surgery.

14. The method of claim 9, further comprising orally administering about 50 mg to about 100 mg tramadol to the human patients about every 6 hours after the human patients no longer requires treatment with intravenous tramadol, until the human patients no longer require treatment with oral tramadol, wherein the tramadol is tramadol base or a pharmaceutically acceptable salt of tramadol.

15. The method of claim 9, wherein a therapeutically effective dose of an intravenous opioid analgesic is administered to the patients (i) at the end of the surgery or (ii) if the human patients request analgesia before the second dose of tramadol.

16. A method of administering tramadol for treating acute pain in human patients via an intravenous dosing regimen comprising intravenously administering a first dose of tramadol to human patients in an amount of about 25 mg;

and thereafter intravenously administering additional doses of tramadol to the human patients in an amount of about 25 mg at dosage intervals of about 4 hours, except that a second dose is intravenously administered as a loading dose at a shortened interval as compared to the dosage interval of about 4 hours, until the patients no longer require treatment with intravenous tramadol, wherein the tramadol is tramadol base or a pharmaceutically acceptable salt of tramadol and a reduction in at least one side-effect associated with tramadol therapy selected from the group consisting of nausea, vomiting, and seizure is achieved.

17. The method of claim 16, wherein the human patients are suffering from acute post-operative pain.

18. The method of claim 16, wherein the dosing regimen provides a Cmax after the third intravenous dose of tramadol 25 mg, and the Cmax of the intravenous dosing regimen after the third intravenous dose of tramadol 25 mg is similar to the steady-state Cmax achieved with an oral tramadol dose of 50 mg administered every 6 hours.

19. The method of claim 16, wherein the intravenous dosing regimen provides a Cmax and AUC of tramadol which is similar to the Cmax and AUC of an oral dose of 50 mg tramadol HCl given every 6 hours at steady-state.

20. The method of claim 16, wherein a therapeutically effective dose of an intravenous opioid analgesic is administered to the patients (i) at the end of the surgery or (ii) if the human patients requests analgesia before the second dose of tramadol.

* * * * *